United States Patent
Valdez et al.

(10) Patent No.: US 10,690,687 B2
(45) Date of Patent: Jun. 23, 2020

(54) PREGABALIN IMMUNOASSAYS

(71) Applicant: ARK Diagnostics, Inc., Fremont, CA (US)

(72) Inventors: Johnny Valdez, Fremont, CA (US); Byung Sook Moon, Palo Alto, CA (US); Alejandro A. Orozco, Gilroy, CA (US); Gonzalo Naranjo, San Martin, CA (US)

(73) Assignee: ARK Diagnostics, Inc., Fremont, CA (US)

(*) Notice: Subject to any disclaimer, the term of this patent is extended or adjusted under 35 U.S.C. 154(b) by 0 days.

(21) Appl. No.: 15/936,158

(22) Filed: Mar. 26, 2018

(65) Prior Publication Data

US 2018/0292421 A1   Oct. 11, 2018

Related U.S. Application Data

(62) Division of application No. 15/045,969, filed on Feb. 17, 2016, now Pat. No. 9,958,464.
(Continued)

(51) Int. Cl.
*G01N 33/94* (2006.01)
*G01N 33/535* (2006.01)
(Continued)

(52) U.S. Cl.
CPC ......... *G01N 33/9406* (2013.01); *A61K 39/00* (2013.01); *C07C 229/04* (2013.01);
(Continued)

(58) Field of Classification Search
CPC .... A61K 39/00; C07C 229/04; C07C 237/22; G01N 33/9406; G01N 33/581;
(Continued)

(56) References Cited

U.S. PATENT DOCUMENTS 3,817,837 A   6/1974   Rubebstein et al.
4,492,762 A   1/1985   Wang et al.
(Continued)

FOREIGN PATENT DOCUMENTS

EP   3067700      9/2016
WO   199006515    6/1990
(Continued)

OTHER PUBLICATIONS

O'sullivan et al. Enzyme immunoassay: a review. Annals of clinical biochemistry 1979, vol. 16, pp. 221-240. (Year: 1979).*
(Continued)

*Primary Examiner* — Shafiqul Haq
(74) *Attorney, Agent, or Firm* — Rudy J. Ng; Bozicevic, Field & Francis LLP

(57) ABSTRACT

Compounds and methods for use in detecting pregabalin in a sample suspected of containing pregabalin are disclosed. Pregabalin derivatives are described for producing pregabalin conjugates. A pregabalin-immunogenic carrier conjugate may be used as an immunogen for the preparation of an anti-pregabalin antibody. A pregabalin-detectable label conjugate may be used in a signal producing system in pregabalin assays.

7 Claims, 5 Drawing Sheets

Related U.S. Application Data

(60) Provisional application No. 62/127,689, filed on Mar. 3, 2015.

(51) Int. Cl.
| | | |
|---|---|---|
| *C07K 16/44* | (2006.01) | |
| *C07C 237/22* | (2006.01) | |
| *C12N 9/96* | (2006.01) | |
| *C12N 9/04* | (2006.01) | |
| *G01N 33/58* | (2006.01) | |
| *A61K 39/00* | (2006.01) | |
| *C07C 229/04* | (2006.01) | |

(52) U.S. Cl.
CPC ............ *C07C 237/22* (2013.01); *C07K 16/44* (2013.01); *C12N 9/0006* (2013.01); *C12N 9/96* (2013.01); *G01N 33/581* (2013.01); *C07K 2317/33* (2013.01); *C12Y 101/01049* (2013.01)

(58) Field of Classification Search
CPC ...... C07K 16/44; C07K 2317/33; C12N 9/96; C12N 9/0006; C12Y 101/01049
See application file for complete search history.

(56) References Cited

U.S. PATENT DOCUMENTS

| | | | |
|---|---|---|---|
| 4,593,089 | A | 6/1986 | Wang et al. |
| 4,668,640 | A | 5/1987 | Wang et al. |
| 4,708,929 | A | 11/1987 | Henderson |
| 4,751,190 | A | 6/1988 | Chiapetta et al. |
| 4,816,567 | A | 3/1989 | Hiratsuka |
| 4,847,195 | A | 7/1989 | Khanna et al. |
| 4,847,209 | A | 7/1989 | Lewis et al. |
| 4,857,453 | A | 9/1989 | Ullman et al. |
| 5,439,798 | A | 8/1995 | Sigler et al. |
| 5,571,728 | A | 11/1996 | Kraus |
| 6,033,890 | A | 3/2000 | Jakobovits et al. |
| 6,090,567 | A | 7/2000 | Jakobovits et al. |
| 6,159,750 | A | 12/2000 | Edmonds |
| 6,203,974 | B1 | 3/2001 | Shah et al. |
| 6,248,597 | B1 | 6/2001 | Eda et al. |
| 6,410,025 | B1 | 6/2002 | Lander |
| 6,455,288 | B1 | 9/2002 | Jakobovits et al. |
| 6,514,770 | B1 | 2/2003 | Sorin |
| 2002/0099092 | A1 | 7/2002 | Blakemore et al. |
| 2010/0292506 | A1 | 11/2010 | Razzetti et al. |
| 2012/0277111 | A1 | 11/2012 | Crabtree et al. |
| 2013/0237899 | A1 | 9/2013 | Pepperberg et al. |
| 2014/0212934 | A1 | 7/2014 | Baynes et al. |

FOREIGN PATENT DOCUMENTS

| | | |
|---|---|---|
| WO | 200232376 | 4/2002 |
| WO | 2008103319 | 8/2008 |
| WO | 2012161798 | 11/2012 |
| WO | 201155291 | 10/2014 |

OTHER PUBLICATIONS

Oellerich, M. Enzyme-immunoassay: a review. J. CLin. Chem. Clin. Biochem. 1984, vol. 22. pp. 895-904. (Year: 1984).*
Hong-Ju et al., (2004) "Effect of gabapentin derivates on mechanical allodynia-like behavior in a rat model of chronic sciatic constriction injury," Bioogranic & Medicinal Chemistry Letter 14(10): 2537-2541.
Horvat et al., (2010) "Synthesis characterization and in vitro pharmacology of novel pregabalin derivatives," European Journal of Medicinal Chemistry 45(4): 1447-1452.
Bauer et al., (2009) "The increased trafficking of the calcium channel subunit alpha2delta-1 to presynaptic terminals in neuropathic pain is inhibited by the alpha2delta ligand pregabalin." J. Neurosci 29(13): 4076-4088.
Buchner et al., (1988) "Cell-specific immune-probes for the brain of normal and mutant *Drosophila melanogaster*1. Wildtype visual system," Cell Tissue Res 253: 357-370.
Chiu et al., (2011) "A Convenient homogeneous enzyme immunoassay for estradiol detection" Biotechnology and Applied Biochemistry 58(1) 75-82.
Krasowski et al., (2009) "Molecular Similarity Methods for Predicting Cross-Reactivity With Therapeutic Drug Monitoring Immunoassays." Therapeutic drug monitoring 31(3): 337-344.
Matute and Streit (1986) "Monoclonal antibodies demonstrating GABA-like immunoreaetivity." Histochemistry 86: 147-157.
Walash et al., (2010) "Simple and sensitive spectrolluorimetfic method for the determination of pregabalin in capsules through derivatization with fluorescamine." Luminescence 26:342-348.
Ahmadkhaniha et al., (2014) "Validated HPLC method for quanification of pregabalin in human plasma using 1-fluoro-2, 4-dinitrobenzene as derivatization agent," Chromatography Research International 1-6.
Gujral et al., (2009) "A novel method for the determination of pregabalin in bulk pharmaceutical formulations and human urine samples" Afican Journal of Pharmacy and Pharmacology, 3(6): 327-334.
Nolli et al., (1991) "Antibodies against the antibiotics: an overview," Ann. 1st. Supper. Sanita 27: 149-154.
Westermann et al., (2002) "Simple, rapid and sensitive determination of epinephrine and norepinephrine in urine and plasma by non-competitive enzyme immunoassay, compared with HPLC method," Clin. Lab 48: 61-71.
Engvall (1980) "Enzyme immunoassay ELISA and EMIT," Methods Enzymol 70:419-439.
Kohler and Milstein, (1975) "Continuous cultures of fused cells secreting antibody of predefined specificity," Nature, 256: 495-497.
McCafferty, et al., (1990) "Phage antibodies: filmentous phage displaying antibody variable domains," Nature 348:552-554.

* cited by examiner

PREGABALIN IMMUNOASSAYS

CROSS-REFERENCE TO RELATED APPLICATION

This application claims priority pursuant to 35 U.S.C. § 119 (e) to the filing date of U.S. Provisional Application Ser. No. 62/127,689 filed on Mar. 3, 2015, the disclosure of which is herein incorporated by reference.

INTRODUCTION

Pregabalin is an analogue of the neurotransmitter gamma amino butyric acid (GABA) with analgesic, anticonsulvant and anxiolytic activity. Pregabalin is described chemically as (S)-3-(aminomethyl)-5-methylhexanoic acid, and its structure is shown below and in FIG. 1, panel A.

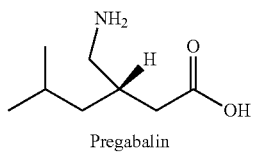

Pregabalin

Pregabalin is indicated for neuropathic pain associated with diabetic peripheral neuropathy, postherpetic neuralgia, adjunctive therapy for adult patients with partial onset seizures, fibromyalgia, neuropathic pain associated with spinal cord injury (see, e.g., LYRICA®). In Europe, pregabalin is also approved to treat generalized anxiety disorder.

Recent reports have suggested that pregabalin is used as a recreational drug and that an abuse potential may exist. Pregabalin is classified as a schedule V drug in the U.S. Drug Enforcement Administration's Controlled Substances Act. In the European Union, Pregabalin is not a controlled substance subjected to special or restricted prescription, but a warning related to its abuse potential was added to the Summary of Product Characteristics in June 2010. Based upon the potential for illicit use of Pregabalin as a recreational drug, urinary drug testing may be a tool to identify its use.

In addition, therapeutic drug management (TDM) of pregabalin can serve as a tool to ensure compliance in administering chemotherapy with the actual prescribed dosage and achievement of effective serum concentration levels. TDM can provide the clinician with insight on patient variation, and allow the clinical to individualize drug dosages to the patient's needs. Successful pain management may be facilitated by consistent monitoring to ensure that the dosage is taken as prescribed.

A variety of analytical methods have been developed for the measurement of pregabalin in blood and urine including gas chromatography coupled with mass spectrometry (GC-MS) and (ultra-) high-performance liquid chromatography coupled with mass spectrometry ((U)HPLC-MS) or fluorometric detection and capillary electrophoresis coupled to time-of-flight mass spectrometry detection (CE/TOF/MS). While chromatographic techniques can be used to determine drug levels, such methods are impractical for commercial use due to, for example, long sample preparation time, long assay time, high cost, and labor-intensive procedures. Immunoassays provide simple and fast analytical methods for detection and measurement of drug levels.

SUMMARY

Methods, compositions and kits are disclosed directed at pregabalin derivatives, immunogens, signal generating moieties, antibodies that bind pregabalin and immunoassays for detection of pregabalin.

Aspects of the present disclosure include a compound of Formula (A):

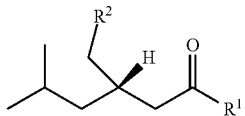

(A)

wherein
$R^1$ or $R^2$ is —X—W-L-Z, wherein
when $R^1$ is —X—W-L-Z, then $R^2$ is —$NH_2$,
when $R^2$ is —X—W-L-Z, then $R^1$ is —OH, and
X is NH;
W is selected from a bond, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and carbonyl;
L is a bond or a linker; and
Z is selected from H, alkyl, substituted alkyl, a reactive functional group, an immunogenic carrier and a detectable label;
or a salt thereof.

In some embodiments, W is a bond. In some embodiments, W is an alkyl or substituted alkyl.

In some embodiments, W is a carbonyl.

In some embodiments, the linking group includes 1-15 carbon atoms and/or 0-6 heteroatoms.

In some embodiments, the linker is selected from:
—$(CH_2)_nC(O)$—,
—$C(O)(CH_2)_n$—,
—$C(O)(CH_2)_nNH$—$C(O)$—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—,
—$C(O)$—$(CH_2)_n$—, and
—$(CH_2)_n$—;
wherein m and n are each independently selected from an integer from 0 to 10.

In some embodiments, Z is an immunogenic carrier. In some embodiments, the immunogenic carrier is a protein. In some embodiments, the protein is selected from the group consisting of hemocyanins, globulins and albumins. In some embodiments, the protein is bovine serum albumin (BSA) or keyhole limpet hemocyanin (KLH). In some embodiments, the immunogenic carrier is a polysaccharide. In some embodiments, Z is a detectable label. In some embodiments, the detectable label is an enzyme. In some embodiments, the enzyme is selected from glucose-6-phosphate dehydrogenase (G6PDH), alkaline phosphatase, β-galactosidase, and horse radish peroxidase. In some embodiments, the enzyme is glucose-6-phosphate dehydrogenase (G6PDH).

In some embodiments, Z is a reactive functional groups selected from halogen, —OH, —SH, —$NH_2$, —O-lower alkyl, epoxy, —S-acyl, carboxyl, maleimidyl, haloacetamide, hydroxysuccinimidyl, succinimidyl, carbonate, anhydride, imidate, an isocyanate, an isothiocyanate, an imidoester, a maleimide, a thiolactone, a diazonium group, an acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, and a photoactivatable group Aspects of the present disclosure include a method for detecting pregabalin. In some embodiments, the method includes: combining in a reaction mixture a sample suspected of containing pregabalin with an antibody that binds pregabalin or a conjugate that includes a compound of the Formula (A) of claim 1; and detecting the presence or absence of a complex that includes the pregabalin and the antibody, where the presence of the complex indicates the presence of pregabalin in the sample.

In some embodiments, the antibody is a polyclonal antibody. In some embodiments, the antibody is a monoclonal antibody. In some embodiments, the antibody has a cross-reactivity with crossreactants of 0.1% or less with respect to binding to pregabalin.

In some embodiments, the reaction mixture includes the conjugate. In some embodiments, the conjugate includes a detectable label.

In some embodiments, the detecting includes determining the presence of an enzymatic reaction product of the conjugate.

Aspects of the present disclosure include an isolated antibody that binds an epitope present in pregabalin and present in a compound of Formula (A) of the present disclosure.

In some embodiments, the antibody is a polyclonal antibody. In some embodiments, the antibody is a monoclonal antibody.

Aspects of the present disclosure include a kit for detecting pregabalin in a sample. The kit includes: an antibody as described herein; and instructions for an assay for detecting pregabalin.

In some embodiments, the kit includes one or more reagents for detecting a complex of the antibody and pregabalin. In some embodiments, the kit includes a compound of Formula (A) of the present disclosure.

DEFINITIONS

Figure 1:
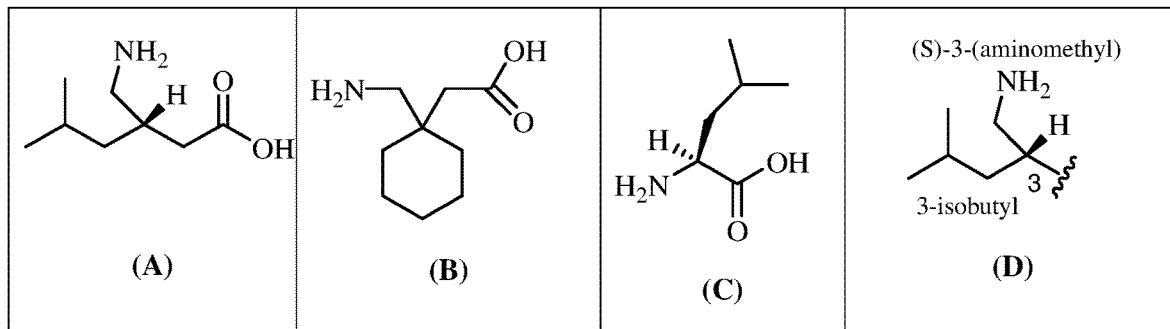
FIG. 1 shows chemical structures of pregabalin [(S)-3-(aminomethyl)-5-methylhexanoic acid](FIG. 1, panel A); gabapentin [2-[1-(aminomethyl)cyclohexyl]acetic acid)] (FIG. 1, panel B); L-leucine (FIG. 1, panel C); and a fragment of pregabalin with the 3-isobutyl group, (S)-3-(aminomethyl) group, and carbon-3 of pregabalin identified (FIG. 1, panel D).

Unless defined otherwise, all technical and scientific terms used herein have the same meaning as commonly understood by one of ordinary skill in the art to which this invention is related. The following terms are defined for purposes of the present disclosure.

An "analyte" is the compound or composition to be measured, the material of interest, such as pregabalin. In certain embodiments, the analyte is a member of a specific binding pair (sbp) and may be a ligand, which is mono- or polyvalent, may be antigenic or haptenic, and is a single compound or plurality of compounds which share at least one common epitopic or determinant site.

Any sample which is reasonably suspected of containing analyte can be analyzed by the methods of the present disclosure. Such samples can include human, animal or man-made samples. The sample can be prepared in any convenient medium which does not interfere with the assay. The sample may be an aqueous solution or a natural fluid, such as, urine, whole blood, serum, plasma, cerebral-spinal fluid, or saliva. In some embodiments, the sample is serum.

"Human serum", as used herein, refers to the aqueous portion of human blood remaining after the fibrin and suspended material (such as cells) have been removed.

A "pregabalin derivative" as used in this disclosure refers to a compound sharing a core structure with pregabalin and that can compete with pregabalin for binding to an anti-pregabalin binding partner, such as an anti-pregabalin antibody.

Certain compounds disclosed herein in connection with embodiments of the present disclosure can exist in unsolvated forms as well as solvated forms, including hydrated forms. In general, the solvated forms are equivalent to unsolvated forms and are encompassed within the reference to the compounds set out in the present disclosure. Certain compounds disclosed herein in connection with embodiments of the present disclosure may exist in multiple crystalline or amorphous forms.

Certain compounds disclosed herein in connection with embodiments of the present disclosure possess asymmetric carbon atoms (optical centers) or double bonds; the racemates, diastereomers, geometric isomers and individual isomers are encompassed within the scope of the present disclosure.

The compounds may be prepared as a single isomer (e.g., enantiomer, cis-trans, positional, diastereomer) or as a mixture of isomers. In certain embodiments, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of ordinary skill in the art to choose an appropriate method for a particular situation. See, generally, Furniss et al. (eds.), Vogel's Encyclopedia of Practical Organic Chemistry, 5th ed., Longman Scientific and Technical Ltd., Essex, 1991, pp. 809-816; and Heller, Acc. Chem. Res. 23: 128 (1990).

Where substituent groups are specified by their conventional chemical formulae, written from left to right, they equally encompass the chemically identical substituents, which would result from writing the structure from right to left, e.g., —CH$_2$O— is intended to also recite —OCH$_2$—. Use of a single dash ("—") or double dash ("—" or "═") refers to a single covalent bond, while use of "═" refers to a double bond. The symbol, )$_2$ or $_2$(, when displayed with —S, indicates that the compound inside the parenthesis may be present as a dimer forming a disulfide bond. The dimer may be reduced to a monomer.

The term "acyl" or "alkanoyl" by itself or in combination with another term, means, unless otherwise stated, a stable straight or branched chain, or cyclic hydrocarbon radical, or combinations thereof, having the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e., C$_1$-C$_{10}$ means one to ten carbons).

Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl.", where "heteroalkyl" refers to carbon chains having one or more substitutions at one or more carbon atoms of the hydrocarbon chain fragment. Alkyl groups that are limited to hydrocarbon groups are termed "homoalkyl". Certain alkyl groups include those containing between about one and about twenty five carbon atoms (e.g. methyl, ethyl and the like).

The term "lower alkyl" generally refers to a straight, branched, or cyclic hydrocarbon chain containing 8 or fewer carbon atoms, and can contain from 1 to 8, from 1 to 6, or from 1 to 4 carbon atoms. Certain "lower alkyl" groups include methyl, ethyl, n-propyl, isopropyl, n-butyl, sec-butyl, tert-butyl, n-pentyl, n-hexyl, n-heptyl and the like. "Lower alkyls" can be optionally substituted at one or more carbon atoms of the hydrocarbon chain.

The terms "alkoxy," "alkylamino" and "alkylthio" (or thioalkoxy) are used to refer to those alkyl groups attached to the remainder of the molecule via an oxygen atom, an amino group, or a sulfur atom, respectively.

By "heteroatom" is meant atoms other than a carbon which may be present in a carbon backbone or a linear, branched or cyclic compound. Certain heteroatoms include oxygen (O), nitrogen (N), sulfur (S), phosphorus (P) and silicon (Si). Heteroatoms can be present in their reduced forms, e.g., —OH, —NH, and —SH.

The term "heteroalkyl," by itself or in combination with another term, means, unless otherwise stated, a straight or branched chain, or cyclic carbon-containing radical, or combinations thereof, having the stated number of carbon atoms and at least one heteroatom which can be a member selected from O, N, Si, P and S, wherein the nitrogen, phosphorous and sulfur atoms are optionally oxidized, and the nitrogen heteroatom is optionally be quaternized. Normally heteroalkyl groups contain no more than two heteroatoms linked in sequence. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Generally, up to two heteroatoms may be consecutive, such as, for example, —CH$_2$—NH—OCH$_3$ and —CH$_2$—O—Si(CH$_3$)$_3$.

Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (usually from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" where each can be independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" can be independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

The term "amino" or "amine group" refers to the group —NR'R" (or N+RR'R") where R, R' and R" are independently selected from hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N+RR'R" and its biologically compatible anionic counterions.

The term "conjugate" refers to a molecule comprised of two or more moieties bound together, optionally through a linking group, to form a single structure. The binding can be made either by a direct connection (e.g., a chemical bond) between the components or by use of a linking group. For example, a pregabalin conjugate generally refers to a chemical compound composed of a pregabalin derivative covalently bound to a moiety of interest, which may be optionally linked through a linking group. In another example, a "pregabalin-enzyme conjugate" refers a pregabalin conjugate having an enzyme as the moiety of interest.

"Conjugation" refers to a process where two subunits are linked together to form a conjugate. The conjugation process can include one or more steps, as described herein.

A "hapten" generally refers to a small molecule that can be specifically bound by an antibody but usually do not induce detectable or significant formation of antibodies unless bound to a carrier protein or other large antigenic molecule. In the context of the present disclosure, pregabalin or a pregabalin derivative may be a hapten.

"Antigen", as used herein, refers to a compound that binds specifically to the variable region or binding site of an antibody. The term "antigen" and "immunogen" may in some cases be used interchangeably.

The term "epitope" refers to a region of an antigen that interacts with an antibody molecule. An antigenic molecule can have one or more epitopes that can be recognized by the same or different antibodies. An epitope or epitopic moiety may include a unique chemical configuration of an antigen, hapten or a reactive ligand. The chemical configuration may be a linear sequence of chemical composition or even a spatial array of chemical groups in the chemical configuration. An epitope is the chemical configuration that associates directly with the binding site in the antibody molecule. The antibody and the chemical group, hapten or reacting ligand containing the epitope form the "specific binding pair" (sbp).

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. In some embodiments, members of a specific binding pair are members of an immunological pair, such as antigen-antibody.

A "ligand" is an organic compound for which a receptor naturally exists or can be prepared. For example, the analyte may be a ligand and embodiments of the present disclosure provide methods for determining the concentration of the ligand.

A "receptor" is a compound or composition capable of recognizing a particular spatial and polar organization of a molecule. These organized areas of a molecule are referred to as epitopic or determinant sites. For example, receptors include, but are not limited to, antibodies and enzymes.

As used herein, the terms "immunogen" and "immunogenic" are meant to refer to substances capable of producing or generating an immune response (e.g., antibody response) in an organism. An immunogen can also be antigen. In some embodiments, the immunogen has a high molecular weight (e.g., greater than 10,000). Thus, a variety of macromolecules such as proteins, lipoproteins, polysaccharides, nucleic acids and teichoic acids can be coupled to a hapten in order to form an immunogen in accordance with embodiments of the present disclosure.

As used herein, the term "immunogenicity" refers to the ability of a molecule to induce an immune response, which is determined both by the intrinsic chemical structure of the molecule and by whether or not the host animal can recognize the compound. Small changes in the structure of an antigen can greatly alter the immunogenicity of a compound and have been used extensively as a general procedure to increase the chances of raising an antibody, particularly against well-conserved antigens. For example, these modification techniques can alter regions of the immunogen to provide better sites for T-cell binding or expose new epitopes for B-cell binding.

A "carrier" or "immunogenic carrier" or "immunogenic moiety" as the terms are used herein, is an immunogenic substance, commonly a polypeptide, that can join with a hapten (such as a pregabalin moiety), thereby enabling the happen to induce an immune response and elicit the production of antibodies that can bind specifically with the antigen (hapten). Carrier substances include, but are not limited to, proteins, peptides (including polypeptides), glycoproteins, saccharides including complex polysaccharides, particles, nucleic acids, polynucleotides, and the like that are recognized as foreign and thereby elicit an immunologic response from the host.

The term "linker" or "linking group" as used in the present disclosure refers to a chemical moiety that connects at least two substructures of a compound, e.g., to provide for covalent connection between a pregabalin hapten and a moiety of interest (e.g., a carrier or detectable label). A linking group has at least one uninterrupted chain of atoms extending between the substructures. The atoms of a linking group are themselves connected by chemical bonds. The number of atoms in a linking group is determined by counting the atoms other than hydrogen. Linking groups can include, but are not limited to, groups such as alkylene, heteroalkylene, cycloalkyl, heterocycloalkyl, aryl, heteroaryl, amino, as described herein.

"Polypeptide" as used herein is meant to encompass a polyaminoacid of any length, and encompasses proteins, protein fragments and peptides. Polypeptides may be genetically encoded or synthetically produced. Polypeptides may also be modified, e.g., by post-translational and/or chemical modification(s).

The term "antibody" includes a protein molecule having one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), epsilon (ε), and alpha (α) which encode the IgM, IgD, IgG, IgE, and IgA isotypes, respectively. "Antibody" as used herein is meant to include full length antibodies and antibody fragments, and may refer to a natural antibody from any organism, an engineered antibody, or an antibody generated recombinantly for experimental, therapeutic, or other purposes as further defined below. Thus, the term "antibody raised against a compound" includes a synthesized antibody or compound having the same structure as an antibody raised against the compound. The term "antibody" includes antibody fragments, as are known in the art, such as Fab, Fab', F(ab')$_2$, Fv, scFv, or other antigen-binding subsequences of antibodies, either produced by the modification of whole antibodies or those synthesized de novo using recombinant DNA technologies. The term "antibody" refers to both monoclonal and polyclonal antibodies. Antibodies can be antagonists, agonists, neutralizing, inhibitory, or stimulatory.

As used herein, the term "polyclonal antibody" refers to a heterogeneous mixture of antibodies with a wide range of specificities and affinities to a given antigen or epitope. Thus, the polyclonal antibody, which can also be referred to as polyclonal antibodies, can include a plurality of antibodies, each distinguishable from the others, that bind or otherwise interact with an antigen. The term "polyclonal" refers to antibodies originating from multiple progenitor cells.

The different antibodies that comprise a polyclonal antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies include hybrid and recombinant antibodies produced by splicing a variable (including hypervariable) domain of an anti-inhibitor antibody with a constant domain, or a light chain with a heavy chain, or a chain from one species with a chain from another species, or fusions with heterologous proteins, regardless of species of origin or immunoglobulin class or subclass designation, as well as antibody fragments, e.g., Fab, F(ab)2, and Fv!, so long as they exhibit the desired biological activity. For example, the monoclonal antibodies may be made by the hybridoma method first described by Kohler & Milstein, Nature, 256:495 (1975), or may be made by recombinant DNA methods (U.S. Pat. No. 4,816,567). The "monoclonal antibodies" may also be isolated from phage libraries generated using the techniques described in, e.g., McCafferty et al., Nature, 348:552-554 (1990).

The term "anti-pregabalin antibody" refers to antibodies that are capable of specifically binding a pregabalin epitope of pregabalin, a pregabalin derivative, or a pregabalin conjugate. "Anti-pregabalin antibodies" include both polyclonal and monoclonal antibodies, as well as antigen-binding fragments thereof as defined above. A "pregabalin epitope" refers to an epitope that is present in pregabalin and in a pregabalin derivative (e.g., a pregabalin conjugate).

The term "binds specifically" or "specifically binds" in the context of antibody binding, refers to high avidity and/or high affinity binding of an antibody to a specific antigen, e.g., to pregabalin. In specific binding under appropriate conditions, antibody binding to pregabalin is stronger than binding of the same antibody to any other epitope, particularly those which may be present in molecules in association with, or in the same sample, as the pregabalin to be detected, e.g., binds more strongly (e.g., higher affinity, higher avidity, or both) to pregabalin than to a non-pregabalin epitope so that by adjusting binding conditions the antibody binds almost exclusively to pregabalin, and not to non-pregabalin moieties that may be present in the sample. Antibodies which bind specifically to pregabalin may be capable of binding other antigens at a weak, yet detectable, level (e.g., 10% or less of the binding shown to pregabalin). Such weak binding, or background binding, is readily discernible from the specific antibody binding to pregabalin, e.g., by use of appropriate controls. "Antibody activity" or "antibody binding activity" in the context of analyte binding assays generally refers to the ability of an antibody to bind a specific antigen in preference to other potential antigens via the antigen combining site located within a variable region of an immunoglobulin.

As used herein, a "detectable label" generally refers to an identifying tag that can provide for a detectable signal, e.g., luminescence (e.g., photoluminescence (e.g., fluorescence, phosphorescence), chemoluminescence (e.g., bioluminescence)), radioactivity, immunodetection, enzymatic activity, and the like).

By "detectably labeled antibody" an antibody (which, as defined above, includes antigen-binding fragments, etc.) having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labelling antibodies, and methods for using labeled antibodies to detect an antigen are well known in the art.

"Antibody complex", "antibody-antigen complex" generally refers to a complex that results following specific binding of an antibody and its antigen, e.g., between an anti-pregabalin antibody and pregabalin (or a pregabalin derivative, e.g., pregabalin conjugate).

An "inhibitory antibody" is an antibody capable of inhibiting the activity of an enzyme or an enzyme-ligand conjugate upon binding an epitope present on the enzyme. Inhibitory antibodies are distinguished from anti-ligand antibodies capable of inhibiting the enzyme activity of enzyme-ligand conjugates upon binding to the ligand.

The term "assessing" includes any form of measurement, and includes determining the presence or absence of an analyte. The terms "assessing", "determining" (e.g., as in "determining the presence or absence of"), "measuring", "evaluating", and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Quantitative, semi-quantitative, and qualitative methods for determining analyte are considered to be methods of measuring the amount of analyte. For example, a qualitative method which merely detects the presence or absence of analyte in a sample suspected of containing an analyte is considered to be included within the scope of the embodiments. Synonyms for the phrase "measuring the amount of analyte" which are contemplated within the scope of the embodiments include, but are not limited to, detecting, measuring, or determining analyte; detecting, measuring, or determining the presence of analyte; and detecting, or determining the amount of analyte.

As used herein, the terms "immunoassay" or "immunodiagnostic" refer to laboratory techniques or test systems that make use of the binding between an antigen or analyte and an antibody in order to identify and/or quantify at least one of the specific antigen or analyte or specific antibody in a biological sample.

As used here, the term "competitive immunoassay" refers to an experimental protocol in which a known amount of an identifiable antigen or analyte competes with another antigen or analyte for binding with an antibody. That is, a known antigen or analyte that binds with a known antibody is combined with a sample that is suspected of containing another antigen or analyte that also binds with the known antibody. This allows for the known antigen or analyte and another antigen or analyte to both compete for the binding site on the antibody. For example, a pregabalin derivative that binds with an anti-pregabalin antibody can be combined with a sample suspected of containing pregabalin, and the pregabalin derivative and pregabalin compete for binding with the anti-pregabalin antibody. The competition for binding with the antibody can then be used to determine whether or not pregabalin is present in the sample, and can further be used to quantify the amount of pregabalin in the sample.

The term "accuracy" refers to the closeness of the agreement between the result of a measurand and a true value of the measurand. The measurand is the substance measured or analyzed, such as the analyte or the ligand entering the binding reaction with the receptor or antibody.

The term "specificity" or "selectivity" refers to the preferential binding of a ligand to a receptor (e.g., antibody). Thus, specificity may refer, in one embodiment, to the degree that pregabalin is bound selectively by an antibody. One measure of the specificity of a receptor to a ligand is crossreactivity. Compounds that cross-react are referred to as "crossreactants." Crossreactants may include compounds having similar chemical structures to pregabalin or a pregabalin derivative. Anti-pregabalin antibodies of the present disclosure include those that bind an epitope of pregabalin, but that do not detectably bind a crossreactants of pregabalin.

The term "sensitivity" is used herein to describe a detection limit, e.g., the smallest amount of an analyte that results in a detectable signal that is distinguishable from a signal obtained in the absence of analyte.

A "reagent" is a substance or compound that is added to a system in order to bring about a chemical reaction, or added to see if a reaction occurs.

As used herein, the term "isolated," when used in the context of an isolated compound, antibody, conjugate, etc., refers to a compound of interest (e.g., a compound as described herein, a conjugate as described herein, an antibody as described herein, etc.) that is in an environment different from that in which the compound naturally occurs. "Isolated" is meant to include compounds of interest (e.g., a compound as described herein, a conjugate as described herein, or an antibody as described herein) that are within samples that are substantially enriched for the compound of interest and/or in which the compound of interest is partially or substantially purified. As used herein, the term "substantially pure" refers to a compound of interest that is removed from its natural environment and is 60% or more free, 75% or more free, 90% or more free, 95% or more free, 98% or more free, or 99% or more free from other components with which it is naturally associated, and/or with which it may be associated during synthesis or production.

DETAILED DESCRIPTION

Before embodiments of the present disclosure are described, it is to be understood that embodiments of the present disclosure are not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the embodiments. The upper and lower limits of these smaller ranges may independently be included or excluded in the range, and each range where either, neither or both limits are included in the smaller ranges is also encompassed within the embodiments, subject to any specifically excluded limit in the stated range. Where the stated range includes one or both of the limits, ranges excluding either or both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can be used in the practice or testing of the embodiments, some methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It is also noted that as used herein and in the appended claims, the singular forms "a", "an", and "the" include plural referents unless the context clearly dictates otherwise. Thus, for example, reference to "a conjugate" includes a plurality of such conjugates and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present application is not entitled to antedate such publication by virtue of prior invention. Further, the dates of publication provided may be different from the actual publication dates which may need to be independently confirmed.

Pregabalin Derivatives

Pregabalin derivatives useful for pregabalin detection are provided in the present disclosure. The term "pregabalin derivatives" is meant to encompass pregabalin-conjugates including immunogens and assay reagents (e.g., detectably labeled conjugates, such as enzyme conjugates, immobilized conjugates, and the like), as well as intermediates useful in production of such pregabalin conjugates. In general, a pregabalin derivative is able to compete with pregabalin for binding to an anti-pregabalin antibody, e.g., in a pregabalin immunoassay. A schematic representation of the structure of pregabalin is shown in FIG. 1, panel A.

Pregabalin and gabapentin are anticonvulsants used in neurology, psychiatry and primary healthcare (FIG. 1, panel A and FIG. 1, panel B, respectively). Pregabalin and gabapentin inhibit calcium influx and subsequent release of excitatory neurotransmitters; however, the compounds differ in their pharmacokinetic and pharmacodynamic characteristics.

Pregabalin is the pharmacologically active S-enantiomer of 3-aminomethyl-5-methyl-hexanoic acid. Embodiments of the present disclosure include a specific immunoassay for pregabalin that has substantially no crossreactivity to gabapentin. In certain embodiments, the chemical structural differences between pregabalin and gabapentin facilitate a reduction in crossreactivity. For example, in certain embodiments, the 3-isobutyl group and/or the (S)-3-(aminomethyl) group of pregabalin may be targeted by an anti-pregabalin antibody (FIG. 1, panel D). In certain embodiments, the 3-isobutyl group and/or the (S)-3-(aminomethyl) group of pregabalin are retained in haptens used to prepare immunogens and raise antibodies accordingly.

Structures of Pregabalin Derivatives

In certain embodiments, compounds (e.g., pregabalin derivatives) of the present disclosure have the general formula (A):

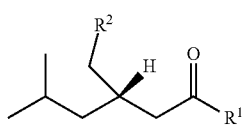

(A)

wherein
  $R^1$ or $R^2$ is —X—W-L-Z, wherein
    when $R^1$ is —X—W-L-Z, then $R^2$ is —$NH_2$,
    when $R^2$ is —X—W-L-Z, then $R^1$ is —OH, and
  X is NH;
  W is selected from a bond, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and carbonyl;
  L is a bond or a linker; and
  Z is selected from H, alkyl, substituted alkyl, a reactive functional group, and a moiety of interest;
  or a salt thereof.

As noted above, the term "linker" as used in the present disclosure refers to a chemical moiety that connects at least two substructures of a compound, e.g., to provide for covalent connection between a pregabalin hapten and a moiety of interest (e.g., a carrier or detectable label). In the context of a pregabalin conjugate, the linker can be a chemical moiety that is the production of a reaction between a reactive functional group and a moiety of interest, e.g., a polypeptide. Linkers include linear or branched, saturated or unsaturated, substituted or unsubstituted, hydrocarbon chains of from 1 to 40 carbon atoms, or from 1 to 20 carbon atoms, or from 1 to 15 carbon atoms, or from 1 to 10 carbon atoms, or from 1 to 6 carbon atoms, which hydrocarbon chains may contain ring structures (e.g., up to two ring structures) and 0-6 heteroatoms, or one or more heteroatoms.

In certain embodiments, W is a bond, such as a bond between X and L. In certain embodiments, W is an alkyl or substituted alkyl. When W of Formula (A) is an alkyl or substituted alkyl, the alkyl or substituted alkyl may be a lower alkyl or substituted lower alkyl group. In some instances, W can be, for example, a straight, branched, or cyclic hydrocarbon chain containing 1 to 8 carbon atoms, from 1 to 6 carbon atoms, or from 1 to 4 carbon atoms.

In certain embodiments, W is selected from alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, W is alkenyl or substituted alkenyl. In certain embodiments, W is alkynyl or substituted alkynyl. In certain embodiments, W is cycloalkyl or substituted cycloalkyl. In certain embodiments, W is heterocyclyl or substituted heterocyclyl. In certain embodiments, W is aryl or substituted aryl. In certain embodiments, W is heteroaryl or substituted heteroaryl.

In certain embodiments, when W of Formula (A) is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is an alkyl (e.g., a lower alkyl) and L is a linker, such as, but not limited to, the following:
  —$(CH_2)_nC(O)$—,
  —$C(O)(CH_2)_n$—,
  —$C(O)(CH_2)_nNH$—$C(O)$—,
  —$C(O)(CH_2)_mNH$—$C(O)(CH_2)_n$—,
  —$(CH_2)_nSCH_2C(O)$—,
  —$(CH_2)_mSCH_2C(O)(CH_2)_n$—,
  —$(CH_2)_mC(O)NH(CH_2)_n$—,
  —$(CH_2)_nNH$—$C(O)$—,
  —$(CH_2)_mNH$—$C(O)(CH_2)_n$—,
  —$C(O)$—$(CH_2)_n$—, and
  —$(CH_2)_n$—;
wherein m and n are each independently selected from an integer from 0 to 10, such as an integer from 1 to 10, or from 1 to 6, or from 1 to 3.

In certain embodiments, W is a carbonyl, and L is a linker, such as, but not limited to, the following:
  —$(CH_2)_nC(O)$—,
  —$(CH_2)_nSCH_2C(O)$—,
  —$(CH_2)_mSCH_2C(O)(CH_2)_n$—,
  —$(CH_2)_mC(O)NH(CH_2)_n$—,
  —$(CH_2)_nNH$—$C(O)$—,
  —$(CH_2)_mNH$—$C(O)(CH_2)_n$—, and
  —$(CH_2)_n$—;
wherein m and n are each independently selected from an integer from 0 to 10, such as an integer from 1 to 10, or from 1 to 6, or from 1 to 3.

In certain embodiments, Z is H, alkyl, substituted alkyl, a reactive functional group, or a moiety of interest. In some embodiments, Z is H. In some embodiments, Z is alkyl or substituted alkyl, such as a $C_{1-10}$ alkyl or $C_{1-10}$ substituted alkyl, or a $C_{1-6}$ alkyl or $C_{1-6}$ substituted alkyl, or a $C_{1-3}$ alkyl or $C_{1-3}$ substituted alkyl.

In certain embodiments, Z is a reactive functional group. A reactive function group is a functional group capable of reacting with a reactive partner to form a covalent bond. In some embodiments, when $R^1$ is —X—W-L-Z, then Z is a reactive functional group, and W is alkyl (e.g., a lower alkyl). In some embodiments, when $R^2$ is —X—W-L-Z, then Z is a reactive functional group, where the reactive functional group is not —OH or —COOH.

In some embodiments, when $R^1$ is —X—W-L-Z, then Z is a reactive functional group and —X—W-L-Z does not include a ring.

When Z of Formula (A) is a reactive functional group (e.g., a reactive functional group capable of reacting with a reactive partner to form a covalent bond), Z can be, for example a halogen (e.g., F, Br, Cl, I, and the like), —OH, —SH, —$NH_2$, —O-lower alkyl, epoxy, —S-acyl, carboxyl, maleimidyl, haloacetamide, hydroxysuccinimidyl, succinimidyl, carbonate, anhydride, imidate, an isocyanate, an isothiocyanate, an imidoester, a maleimide, a thiolactone, a diazonium group, an acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, or a photoactivatable group.

In certain embodiments of Formula (A), Z is a moiety of interest. For example, moieties of interest for Z of Formula (A) include immunogenic carriers (e.g., carrier proteins) and detectable labels. Moieties of interest are described in more detail below.

In some embodiments, the moiety of interest is a peptide, such as a polypeptide. In these embodiments, the moiety of interest is not a single amino acid residue, but may be a polyamino acid chain (i.e., polypeptide). In some embodiments, the moiety of interest is not a bile acid. In some embodiments where the moiety of interest is a polypeptide, the polypeptide is other than a transporter protein. In some embodiments, the pregabalin derivative is not a bile acid conjugate. In some embodiments, the moiety of interest is not a bile acid.

In certain embodiments, the pregabalin derivative is a salt of a pregabalin derivative. Salts of pregabalin derivatives include, but are not limited to, alkali metal salts, such as (sodium salts, potassium salts, magnesium salts, etc.), halide salts (e.g., bromo, chloro, and the like), acetate salts (e.g., salts with trifluoroacetic acid, and the like), combinations thereof, and the like.

Pregabalin derivatives can be further described as having a formula selected from Formula A1 and Formula A2:

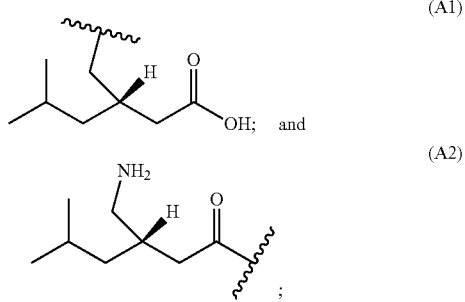

wherein the wavy line ("~~~") indicates the point at which the pregabalin moiety is attached to the remainder of the pregabalin derivative, e.g., attached through one or more chemical moieties to a moiety of interest, e.g., a pregabalin conjugate, e.g., a pregabalin conjugate having a immunogenic carrier or a detectable label. For example, the wavy line can represent a site of attachment to a polypeptide, detectable label, solid support, and the like, where attachment can be through a chemical structure as set out above.

Further examples of pregabalin derivatives are described below.

Pregabalin Derivatives of Formula (I)

In some embodiments, the pregabalin derivative is of Formula (I) below, in which the pregabalin derivative includes an extension from the amine group of pregabalin or its salt:

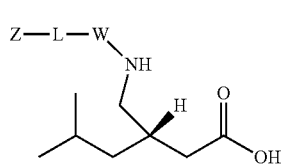

wherein W, L, and Z can be as defined above in Formula (A), and can be any combinations exemplified for Formula (A) as set out above. Accordingly, when W of Formula (I) is alkyl (e.g., a lower alkyl group), W can be, for example, a straight, branched, or cyclic hydrocarbon chain containing 1 to 8 carbon atoms, from 1 to 6 carbon atoms, or from 1 to 4 carbon atoms. In some instances, when W of Formula (I) is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is a bond, such as a bond between L and the —NH— group of the pregabalin derivative. In certain embodiments, W is an alkyl or substituted alkyl. When W of Formula (I) is an alkyl or substituted alkyl, the alkyl or substituted alkyl may be a lower alkyl or substituted lower alkyl group. In some instances, W can be, for example, a straight, branched, or cyclic hydrocarbon chain containing 1 to 8 carbon atoms, from 1 to 6 carbon atoms, or from 1 to 4 carbon atoms.

In certain embodiments, W is selected from alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, W is alkenyl or substituted alkenyl. In certain embodiments, W is alkynyl or substituted alkynyl. In certain embodiments, W is cycloalkyl or substituted cycloalkyl. In certain embodiments, W is heterocyclyl or substituted heterocyclyl. In certain embodiments, W is aryl or substituted aryl. In certain embodiments, W is heteroaryl or substituted heteroaryl.

In certain embodiments, when W of Formula (I) is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is an alkyl (e.g., a lower alkyl) and L is a linker, such as, but not limited to, the following:
—(CH$_2$)$_n$C(O)—,
—C(O)(CH$_2$)$_n$—,
—C(O)(CH$_2$)$_n$NH—C(O)—,
—C(O)(CH$_2$)$_m$NH—C(O)(CH$_2$)$_n$—,
—(CH$_2$)$_n$SCH$_2$C(O)—,
—(CH$_2$)$_m$SCH$_2$C(O)(CH$_2$)$_n$—,
—(CH$_2$)$_m$C(O)NH(CH$_2$)$_n$—,
—(CH$_2$)$_n$NH—C(O)—,
—(CH$_2$)$_m$NH—C(O)(CH$_2$)$_n$—,
—C(O)—(CH$_2$)$_n$—, and
—(CH$_2$)$_n$—;
wherein m and n are each independently selected from an integer from 0 to 10, such as an integer from 1 to 10, or from 1 to 6, or from 1 to 3.

In certain embodiments, W is a carbonyl, and L is a linker, such as, but not limited to, the following:
—(CH$_2$)$_n$C(O)—,
—(CH$_2$)$_n$SCH$_2$C(O)—,
—(CH$_2$)$_m$SCH$_2$C(O)(CH$_2$)$_n$—,
—(CH$_2$)$_m$C(O)NH(CH$_2$)$_n$—,
—(CH$_2$)$_n$NH—C(O)—,
—(CH$_2$)$_m$NH—C(O)(CH$_2$)$_n$—, and
—(CH$_2$)$_n$—;

wherein m and n are each independently selected from an integer from 0 to 10, such as an integer from 1 to 10, or from 1 to 6, or from 1 to 3.

In certain embodiments, Z is H, alkyl, substituted alkyl, a reactive functional group, or a moiety of interest. In some embodiments, Z is H. In some embodiments, Z is alkyl or substituted alkyl, such as a $C_{1\text{-}10}$ alkyl or $C_{1\text{-}10}$ substituted alkyl, or a $C_{1\text{-}6}$ alkyl or $C_{1\text{-}6}$ substituted alkyl, or a $C_{1\text{-}3}$ alkyl or $C_{1\text{-}3}$ substituted alkyl.

In certain embodiments, Z is a reactive functional group. When Z of Formula (I) is a reactive functional group (e.g. a reactive functional group capable of reacting with a reactive partner to form a covalent bond), Z can be, for example a halogen (e.g., F, Br, Cl, I, and the like), —OH, —SH, —NH$_2$, —O-lower alkyl, epoxy, —S-acyl, carboxyl, maleimidyl, haloacetamide, hydroxysuccinimidyl, succinimidyl, carbonate, anhydride, imidate, an isocyanate, an isothiocyanate, an imidoester, a maleimide, a thiolactone, a diazonium group, an acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, or a photoactivatable group. Reactive functional groups for Z can be any of those as exemplified for Z of Formula (A) described herein.

In certain embodiments, Z is a moiety of interest. For example, moieties of interest for Z of Formula (I) include immunogenic carriers (e.g., carrier proteins) and detectable labels. Examples of moieties of interest are described in more detail as related to Formula (A) above.

In certain embodiments, —W-L-Z of Formula (I) may be selected from —(CH$_2$)$_m$—SH, —CO—(CH$_2$)$_n$—Br, and —(CH$_2$)$_o$—S—CH$_2$—CO—CH$_2$—Br, where m, n, and o are each independently selected from 1, 2 or 3.

Figure 2:
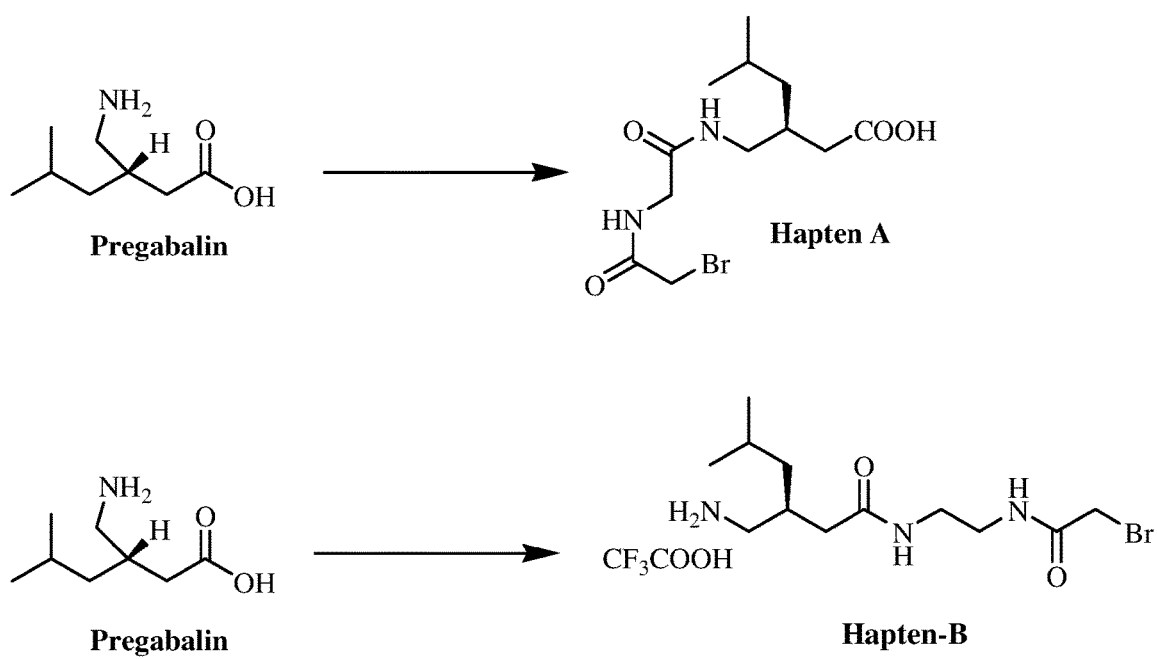
FIG. 2 is a schematic showing the structures of pregabalin derivatives, Hapten-A and Hapten-B, according to embodiments of the present disclosure.

Examples of pregabalin derivatives of Formula (I) are provided in FIG. 2, such as pregabalin Hapten-A. In pregabalin Hapten-A, W is carbonyl, L is —(CH$_2$)NH—C(O)(CH$_2$)—, and Z is Br.

Salts of pregabalin derivative of Formula (I) include those as described above for Formula (A).

Pregabalin Derivatives of Formula II

In some embodiments, pregabalin derivatives are characterized by an extension from the carbonyl group of pregabalin or its salt, which can be described by Formula (II):

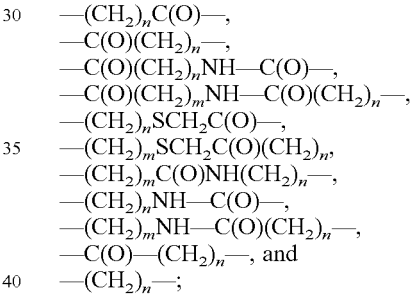

(II)

wherein W, L, and Z can be as defined above in Formula (A), and can be any combinations exemplified for Formula (A) as set out above. Accordingly, when W of Formula (II) is alkyl (e.g., a lower alkyl group), W can be, for example, a straight, branched, or cyclic hydrocarbon chain containing 1 to 8 carbon atoms, from 1 to 6 carbon atoms, or from 1 to 4 carbon atoms. In some instances, when W of Formula (II) is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is a bond, such as a bond between L and the —NH— group of the pregabalin derivative. In certain embodiments, W is an alkyl or substituted alkyl. When W of Formula (II) is an alkyl or substituted alkyl, the alkyl or substituted alkyl may be a lower alkyl or substituted lower alkyl group. In some instances, W can be, for example, a straight, branched, or cyclic hydrocarbon chain containing 1 to 8 carbon atoms, from 1 to 6 carbon atoms, or from 1 to 4 carbon atoms.

In certain embodiments, W is selected from alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, W is alkenyl or substituted alkenyl. In certain embodiments, W is alkynyl or substituted alkynyl. In certain embodiments, W is cycloalkyl or substituted cycloalkyl. In certain embodiments, W is heterocyclyl or substituted heterocyclyl. In certain embodiments, W is aryl or substituted aryl. In certain embodiments, W is heteroaryl or substituted heteroaryl.

In certain embodiments, when W of Formula (II) is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is an alkyl (e.g., a lower alkyl) and L is a linker, such as, but not limited to, the following:
—(CH$_2$)$_n$C(O)—,
—C(O)(CH$_2$)$_n$—,
—C(O)(CH$_2$)$_n$NH—C(O)—,
—C(O)(CH$_2$)$_m$NH—C(O)(CH$_2$)$_n$—,
—(CH$_2$)$_n$SCH$_2$C(O)—,
—(CH$_2$)$_m$SCH$_2$C(O)(CH$_2$)$_n$,
—(CH$_2$)$_m$C(O)NH(CH$_2$)$_n$,
—(CH$_2$)$_n$NH—C(O)—,
—(CH$_2$)$_m$NH—C(O)(CH$_2$)$_n$—,
—C(O)—(CH$_2$)$_n$—, and
—(CH$_2$)$_n$—;
wherein m and n are each independently selected from an integer from 0 to 10, such as an integer from 1 to 10, or from 1 to 6, or from 1 to 3.

In certain embodiments, W is a carbonyl, and L is a linker, such as, but not limited to, the following:
—(CH$_2$)$_n$C(O)—,
—(CH$_2$)$_n$SCH$_2$C(O)—,
—(CH$_2$)$_m$SCH$_2$C(O)(CH$_2$)$_n$—,
—(CH$_2$)$_m$C(O)NH(CH$_2$)$_n$—,
—(CH$_2$)$_n$NH—C(O)—,
—(CH$_2$)$_m$NH—C(O)(CH$_2$)$_n$—, and
—(CH$_2$)$_n$—;
wherein m and n are each independently selected from an integer from 0 to 10, such as an integer from 1 to 10, or from 1 to 6, or from 1 to 3.

In certain embodiments, Z is H, alkyl, substituted alkyl, a reactive functional group, or a moiety of interest. In some embodiments, Z is H. In some embodiments, Z is alkyl or substituted alkyl, such as a $C_{1\text{-}10}$ alkyl or $C_{1\text{-}10}$ substituted alkyl, or a $C_{1\text{-}6}$ alkyl or $C_{1\text{-}6}$ substituted alkyl, or a $C_{1\text{-}3}$ alkyl or $C_{1\text{-}3}$ substituted alkyl.

In certain embodiments, Z is a reactive functional group. When Z of Formula (II) is a reactive functional group (e.g., a reactive functional group capable of reacting with a reactive partner to form a covalent bond), Z can be, for example a halogen (e.g., F, Br, Cl, I, and the like), —OH, —SH, —NH$_2$, —O-lower alkyl, epoxy, —S-acyl, carboxyl, maleimidyl, haloacetamide, hydroxysuccinimidyl, succinimidyl, carbonate, anhydride, imidate, an isocyanate, an isothiocyanate, an imidoester, a maleimide, a thiolactone, a diazonium group, an acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, or a photoactivatable group. Reactive functional groups for Z can be any of those as exemplified for Z of Formula (A) described herein.

In certain embodiments, Z is a moiety of interest. For example, moieties of interest for Z of Formula (II) include immunogenic carriers (e.g., carrier proteins) and detectable labels. Examples of moieties of interest are described in more detail below as related to Formula (A) above.

In certain embodiments, —W-L-Z of Formula (II) may be selected from —(CH$_2$)$_m$—SH, —CO—(CH$_2$)$_n$—Br, or —(CH$_2$)$_o$—S—CH$_2$—CO—CH$_2$—Br, where m, n, and o are each independently selected from 1, 2 or 3.

Examples of pregabalin derivatives of Formula (II) are provided in FIG. 2, such as pregabalin Hapten-B. In pregabalin Hapten-B, W is a bond, L is —(CH$_2$)$_2$NH—C(O)(CH$_2$)—, and Z is Br.

Salts of pregabalin derivatives of Formula (II) include those as described above for Formula (A).

Methods of Making Pregabalin Derivatives

The compounds of the present disclosure are synthesized by an appropriate combination of generally known synthetic methods. Techniques useful in synthesizing the compounds of the present disclosure are generally known those of skill in the relevant art. The discussion below is offered to illustrate examples of certain methods available for use in synthesizing the compounds of the present disclosure, and is not intended to limit the scope of reactions or reaction sequences that are useful in preparing the compounds of the present disclosure.

In certain embodiments, compounds of the present disclosure are synthesized as described herein. For example, Hapten-A, which includes an amine modified derivative of pregabalin may be synthesized according to Scheme 1 as described below.

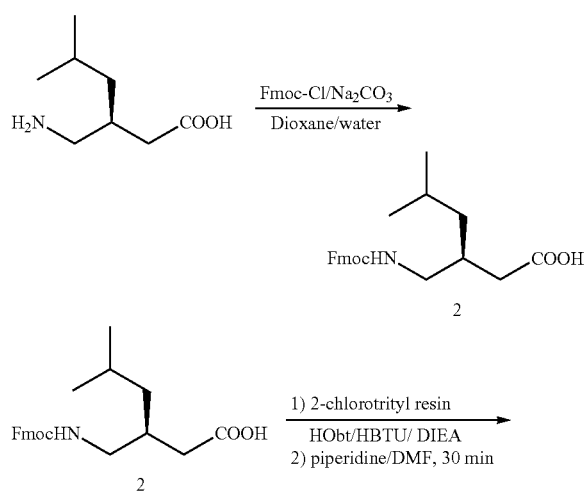

Scheme 1

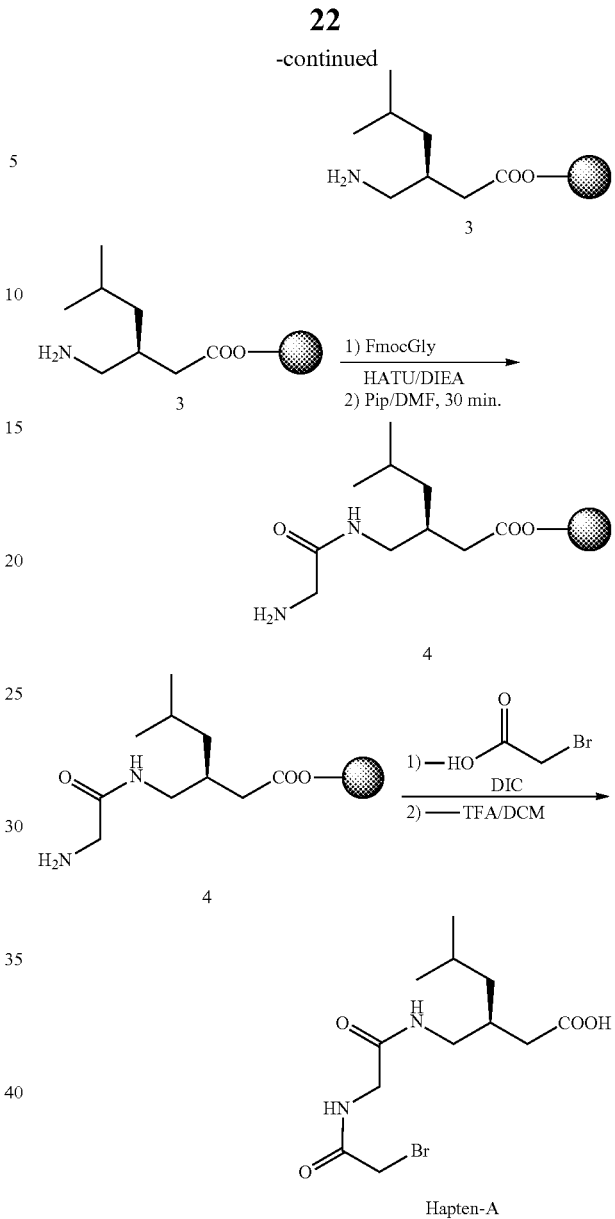

Hapten-A

In certain embodiments, pregabalin may be taken into an aqueous solution of sodium carbonate and cooled in ice bath. A solution of Fmoc-Cl in dioxane may be added. The reaction can be allowed to warm up to room temperature and stirred. In certain embodiments, water is added and extracted with ethyl acetate. The water layer may be cooled (e.g., in an ice bath) and acidified to pH=1 with an acid (e.g., HCl), then extracted with ethyl acetate (3×50 ml). The combined organic layer may be washed with brine, dried over MgSO$_4$, and concentrated to give a crude product. The crude product may be purified on silica gel using ethyl acetate in hexane to give intermediate compound 2.

In certain embodiments, Fmoc-pregabalin (compound 2) and N,N-diisopropylethylamine (DIEA) are mixed in dichloromethane (DCM) and added to 2-chlorotrityl resin. After one hour of shaking, methanol may be added and mixed. Resulting compound 3 may be drained, washed successively with DCM and dimethylformamide (DMF). In certain embodiments, a solution of piperidine in DMF is added to compound 3 and shaken. The reactions may be drained and washed as described above. In certain embodiments, compound 3 is dried under vacuum and used for the next step.

In certain embodiments, Fmoc-glycine and 1-[bis(dimethylamino)methylene]-1H-1,2,3-triazolo[4,5-b]pyridinium 3-oxid hexafluorophosphate (HATU) are added to a mixture of compound 3 in DMF. In certain embodiments, DIEA is added and shaken. The reaction may be repeated twice. In certain embodiments, the resin is drained and washed with DMF, DCM and MeOH. A solution of piperidine/DMF may be added and shaken. In certain embodiments, resulting compound 4 is drained and washed as described above and dried under vacuum.

In certain embodiments, to a solution of 2-bromoacetic acid in dry DMF is added N,N'-diisopropylcarbodiimide (DIC). In certain embodiments, compound 4 is added to the mixture and shaken. This reaction may be repeated twice. The resulting crude product may be drained and washed with DMF, DCM, and methanol. The crude product may then be dried under vacuum. In certain embodiments, the crude product is taken in DCM and trifluoroacetic acid (TFA) is added and shaken. The crude product may be drained and washed with TFA/DCM solution. The combined drained and wash solution may be evaporated to dryness and triturated with ether. In certain embodiments, the crude product is purified on silica gel using methanol in DCM to give an amine modified derivative of pregabalin, Hapten-A.

In certain embodiments, Hapten-B, which includes a carboxylic acid modified derivative of pregabalin may be synthesized according to Scheme 2 as described below.

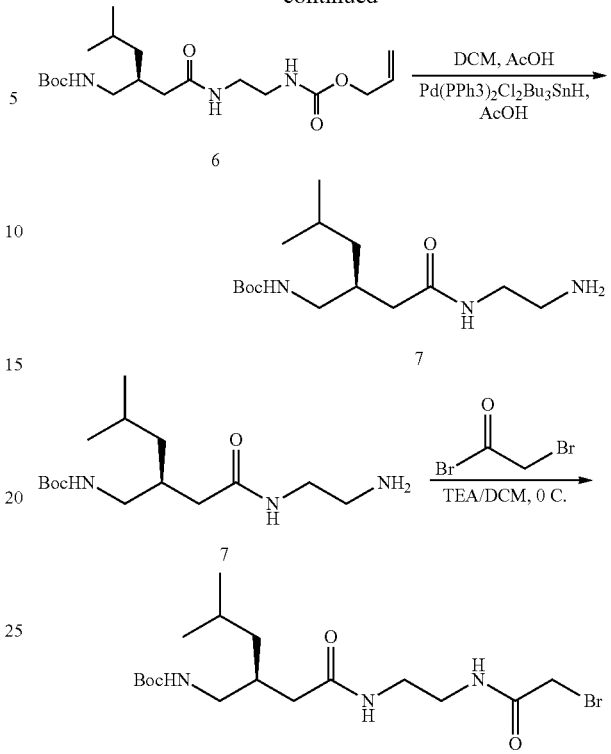

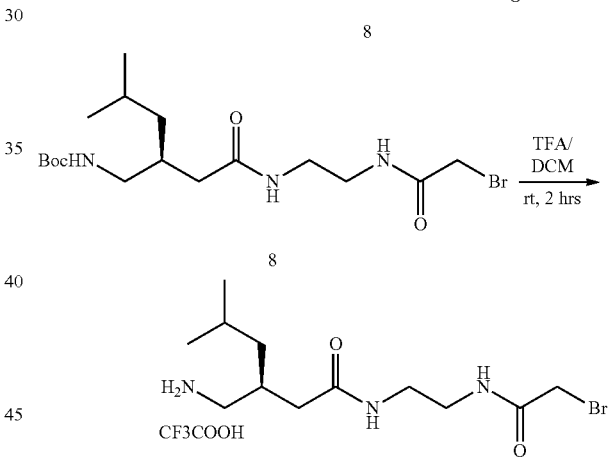

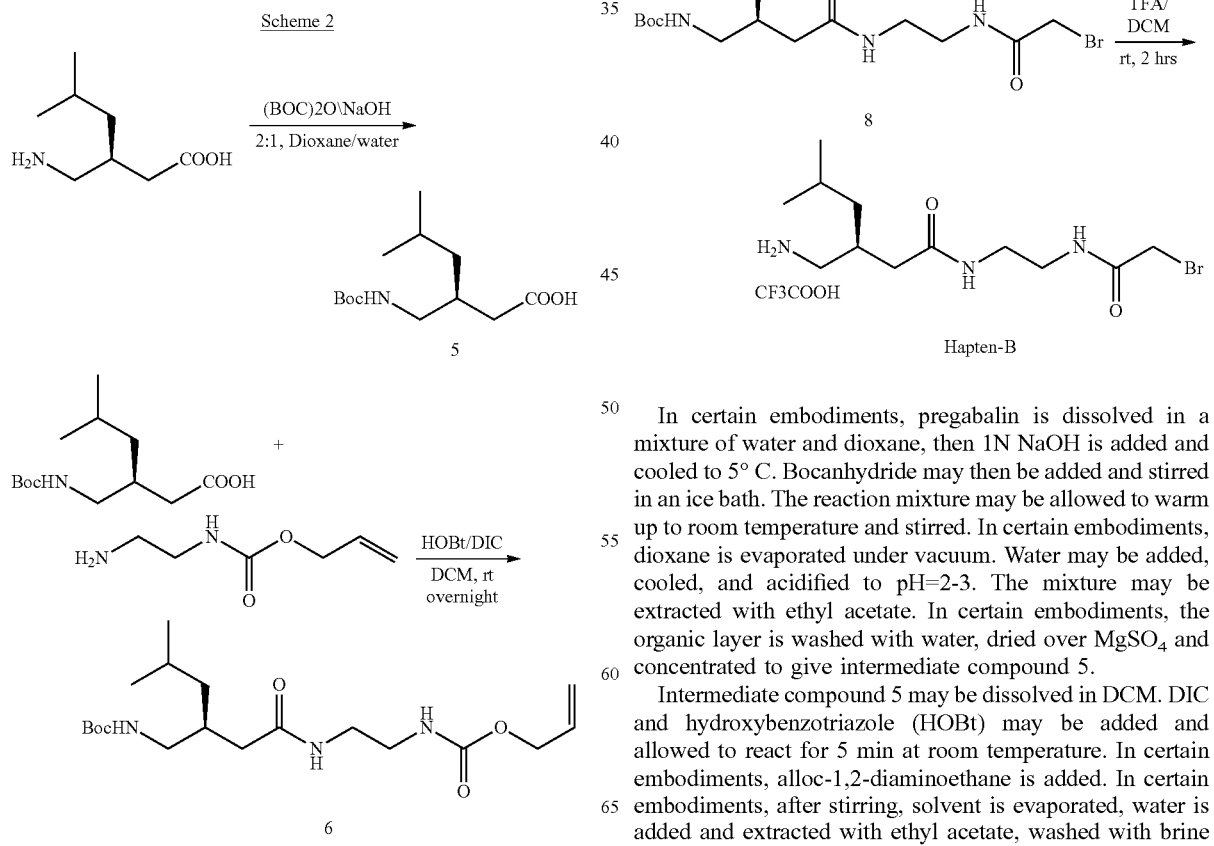

In certain embodiments, pregabalin is dissolved in a mixture of water and dioxane, then 1N NaOH is added and cooled to 5° C. Bocanhydride may then be added and stirred in an ice bath. The reaction mixture may be allowed to warm up to room temperature and stirred. In certain embodiments, dioxane is evaporated under vacuum. Water may be added, cooled, and acidified to pH=2-3. The mixture may be extracted with ethyl acetate. In certain embodiments, the organic layer is washed with water, dried over MgSO$_4$ and concentrated to give intermediate compound 5.

Intermediate compound 5 may be dissolved in DCM. DIC and hydroxybenzotriazole (HOBt) may be added and allowed to react for 5 min at room temperature. In certain embodiments, alloc-1,2-diaminoethane is added. In certain embodiments, after stirring, solvent is evaporated, water is added and extracted with ethyl acetate, washed with brine and dried over MgSO$_4$. After evaporation of solvent, crude product may be obtained, which can be purified on silica gel using methanol in DCM to give compound 6.

In certain embodiments, compound 6 is dissolved in DCM. Dichlorobis(triphenylphosphine) palladium(II) can be added followed by tributyltinhydride and acetic acid. After overnight stirring, more palladium catalyst may be added and stirred. In certain embodiments, the presence or absence of starting material is detected by thin layer chromatography (TLC). Solvent may be evaporated and the crude product can be triturated in ether and decanted. In certain embodiments, the crude product is left under high vacuum for 2 hrs. This material can then be dissolved in DCM and hexane and left at 4° C. overnight. In certain embodiments, solvent is decanted and the solid colorless precipitate left under vacuum to give compound 7. In certain embodiments, compound 7 may be used in the next step without further purification.

In certain embodiments, compound 7 in DCM is cooled and triethylamine is added, followed by bromoacethyl bromide. The reaction mixture may be stirred in an ice bath until no starting material remains (e.g., as monitored by TLC). In certain embodiments, solvent is removed under vacuum, and water is added and extracted with ethyl acetate. In certain embodiments, the organic layer is dried over $MgSO_4$ and concentrated to give crude product, which can be purified on silica gel using ethyl acetate/hexanes to give compound 8.

In certain embodiments, to a solution of compound 8 in DCM, is added TFA at room temperature and stirred. In certain embodiments, after TLC shows no remaining starting material, solvent is evaporated under vacuum and the crude product is triturated with ether. In certain embodiments, the product is left under vacuum to give a carboxylic acid modified derivative of pregabalin, Hapten-B.

Pregabalin Conjugates

In certain embodiments, a pregabalin conjugate includes a pregabalin moiety and a covalently bound moiety of interest, where the pregabalin moiety and moiety of interest can be covalently bound as a result of reaction through a reactive functional group of the pregabalin derivative. Pregabalin conjugates of the present disclosure are thus of the general Formula (A'):

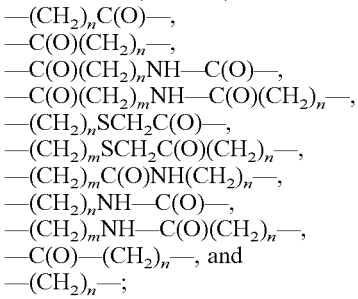

(A')

wherein
$R^1$ or $R^2$ is —X—W-L-Z, wherein
when $R^1$ is —X—W-L-Z, then $R^2$ is —$NH_2$,
when $R^2$ is —X—W-L-Z, then $R^1$ is —OH, and
X is NH;
W is selected from a bond, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and carbonyl;
L is a bond or a linker; and
Z is a moiety of interest (e.g., an immunogenic carrier or a detectable label);
or a salt thereof.

In some instances, when W of Formula (A') is alkyl (e.g., a lower alkyl group), W can be, for example, a straight, branched, or cyclic hydrocarbon chain containing 1 to 8 carbon atoms, from 1 to 6 carbon atoms, or from 1 to 4 carbon atoms. In some instances, when W of Formula (A') is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chains may contain ring structures (e.g., up to two ring structures) and one or more heteroatoms.

In certain embodiments, W is selected from alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, W is alkenyl or substituted alkenyl. In certain embodiments, W is alkynyl or substituted alkynyl. In certain embodiments, W is cycloalkyl or substituted cycloalkyl. In certain embodiments, W is heterocyclyl or substituted heterocyclyl. In certain embodiments, W is aryl or substituted aryl. In certain embodiments, W is heteroaryl or substituted heteroaryl.

In certain embodiments, when W of Formula (A') is a carbonyl group, then L is a linker, which can be, for example, a hydrocarbon chain of from 1 to 40 carbon atoms, or from 1 to 20 carbon atoms, or from 1 to 10 carbon atoms, or from 1 to 6 carbon atoms, which hydrocarbon chain may optionally contain ring structures (e.g., up to two ring structures) and one or more heteroatoms.

In certain embodiments, W is an alkyl (e.g., a lower alkyl) and L is a linker, such as, but not limited to, the following:
—$(CH_2)_nC(O)$—,
—$C(O)(CH_2)_n$—,
—$C(O)(CH_2)_nNH$—$C(O)$—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—,
—$C(O)$—$(CH_2)_n$—, and
—$(CH_2)_n$—;

wherein m and n are each independently selected from an integer from 0 to 10, such as an integer from 1 to 10, or from 1 to 6, or from 1 to 3.

In certain embodiments, W is a carbonyl, and L is a linker, such as, but not limited to, the following:
—$(CH_2)_nC(O)$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—, and
—$(CH_2)_n$—;

wherein m and n are each independently selected from an integer from 0 to 10, such as an integer from 1 to 10, or from 1 to 6, or from 1 to 3.

In certain embodiments of Formula (A'), Z is a moiety of interest. For example, moieties of interest for Z of Formula (A') include immunogenic carriers (e.g., carrier proteins) and detectable labels. Moieties of interest are described in more detail below.

In some embodiments, the moiety of interest is a peptide, such as a polypeptide. In these embodiments, the moiety of interest is not a single amino acid residue, but may be a polyamino acid chain (i.e., polypeptide). In some embodiments, the moiety of interest is not a bile acid. In some embodiments where the moiety of interest is a polypeptide, the polypeptide is other than a transporter protein. In some embodiments, the pregabalin derivative is not a bile acid conjugate. In some embodiments, the moiety of interest is not a bile acid.

In certain embodiments, the pregabalin derivative is a salt of a pregabalin derivative. Salts of pregabalin derivatives include, but are not limited to, alkali metal salts, such as (sodium salts, potassium salts, magnesium salts, etc.), halide salts (e.g., bromo, chloro, and the like), acetate salts (e.g., salts with trifluoroacetic acid, and the like), combinations thereof, and the like.

In certain embodiments, the moiety of interest is bound to the pregabalin conjugate through a linking group selected from —CONH—, —NHCO—, —NHCONH—, —NH—(C=S)—NH—, —O—CO—NH—, —NH—O—CO—, —S—, —NH—(C=NH)—, —N=N—, and —NH—.

The present disclosure also provides pregabalin conjugates of the Formula (I'):

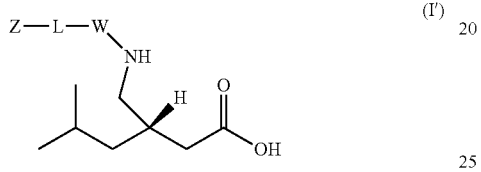

(I')

wherein W and L are as defined in Formula (A') above, and Z is a moiety of interest.

In some instances, linkers for pregabalin conjugates of Formula (I') are as described above in Formula (A'). Salts of pregabalin conjugate of Formula (I') can include those as described for Formula (A') above.

Figure 5:
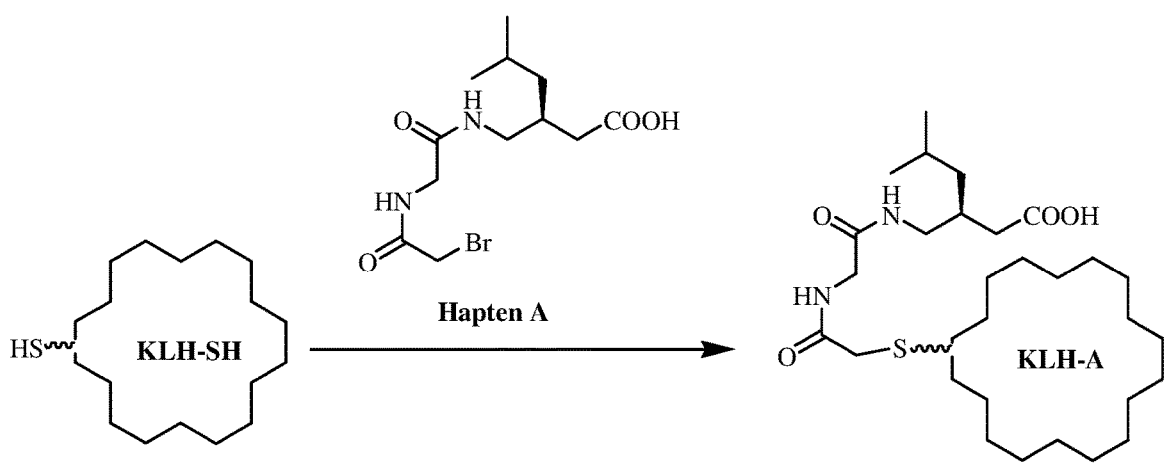
FIG. 5 is a schematic of the structures of a pregabalin conjugate including KLH-A, where pregabalin derivative Hapten-A is conjugated with KLH-SH, according to embodiments of the present disclosure.
Figure 7:
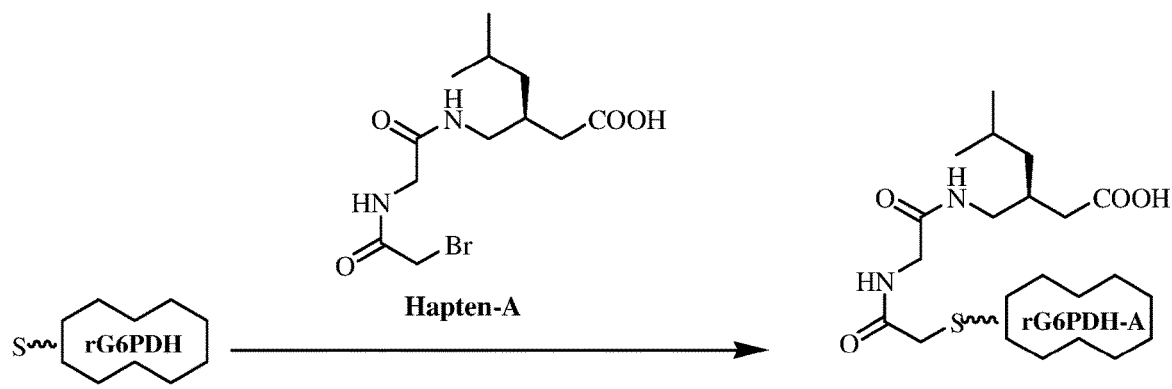
FIG. 7 is a schematic representation of rG6PDH and the structures of a pregabalin conjugate including rG6PDH-A, where pregabalin derivative Hapten-A is conjugated with rG6PDH, according to embodiments of the present disclosure.

Examples of pregabalin conjugates of Formula (I') are provided in FIG. 5 and FIG. 7, such as pregabalin conjugates KLH-A and rG6PDH-A. In Conjugates KLH-A and rG6PDH-A, W is a carbonyl, L is —(CH$_2$)(NH)(C=O)(CH$_2$)—, and Z is a carrier protein (e.g., KLH), which is attached to the pregabalin moiety through a sulfhydryl group of the protein or a sulfhydryl of a cysteine residue of the protein (e.g., through a sulfide bond).

In certain embodiments, pregabalin conjugates are characterized by an extension from the carbonyl group of pregabalin, which can be described by Formula (II'):

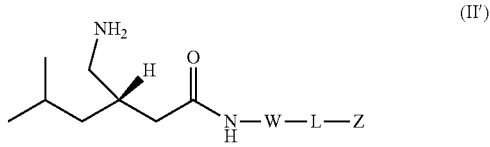

(II')

wherein W and L are as defined in Formula (A') above, and Z is a moiety of interest.

In some instances, linkers for pregabalin conjugates of Formula (II') are as described above in Formula (A'). Salts of pregabalin conjugates of Formula (II') can include those as described above for Formula (A').

Figure 6:
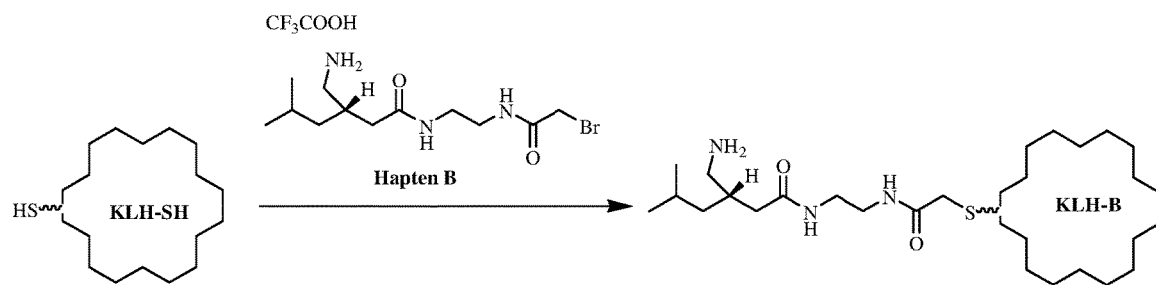
FIG. 6 is a schematic of the structures of a pregabalin conjugate including KLH-B, where pregabalin derivative Hapten-B is conjugated with KLH-SH, according to embodiments of the present disclosure.
Figure 8:
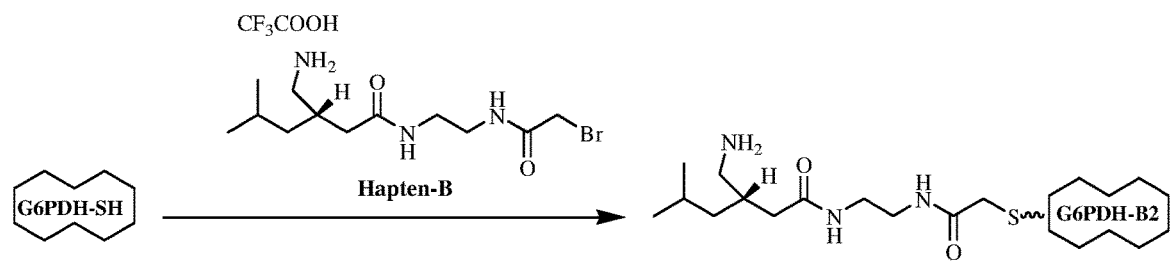
FIG. 8 is a schematic representation of native G6PDH and the structures of a pregabalin conjugate including G6PDH-B, where pregabalin derivative Hapten-B is conjugated with G6PDH, according to embodiments of the present disclosure.
Figure 9:
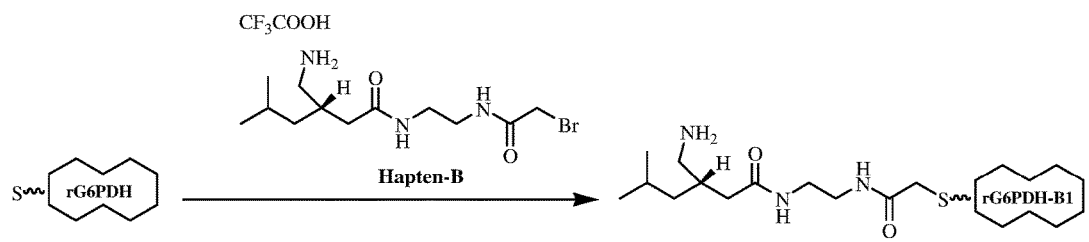
FIG. 9 is a schematic representation of rG6PDH and the structures of a pregabalin conjugate including recombinant rG6PDH-B, where pregabalin derivative Hapten-B is conjugated with rG6PDH, according to embodiments of the present disclosure.

Examples of pregabalin conjugates of Formula (II') are provided in FIG. 6, FIG. 8 and FIG. 9, such as Conjugates KLH-B, G6PDH-B2, and rG6PDH-B1, respectively. In Conjugates KLH-B, rG6PDH-B1 and G6PDH-B2, W is a bond, L is —(CH$_2$)$_2$(NH)—(C=O)(CH$_2$)—, and Z is a carrier protein (e.g., KLH), which is attached to the pregabalin moiety through a sulfhydryl group of the protein or a sulfhydryl of a cysteine residue of the protein (e.g., through a sulfide bond).

In certain embodiments, where the moiety of interest has multiple available covalent attachment sites for a pregabalin moiety (e.g., a reactive partner having multiple reaction sites for reaction with a pregabalin derivative), the pregabalin conjugate can include more than one pregabalin moiety. Accordingly, pregabalin conjugates of the present disclosure include those in which two or more, pregabalin moieties are bound to the same moiety of interest (e.g., polypeptide (e.g., carrier protein), solid support (e.g., Sepharose® bead, particle (e.g., gold particle, magnetic particle)). Such pregabalin conjugates can be represented by Formula (I''') or Formula (II''') as follows:

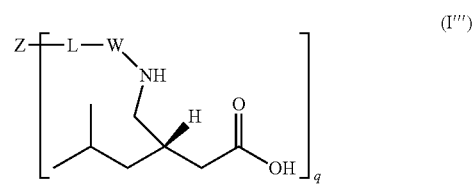

(I''')

wherein W and L are as defined in Formula (A') above, and Z is a moiety of interest having two or more attachment sites for a pregabalin moiety; or

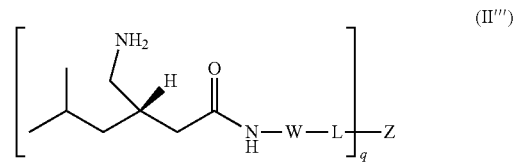

(II''')

wherein W and L are as defined in Formula (A') above, and Z is a moiety of interest having two or more attachment sites for a pregabalin moiety; and wherein q is 1 or more, such as 2 or more, 5 or more, or 10 or more, 15 or more, up to a number of reaction sites available on Z. For example, where Z is a polypeptide, q can be up to the number of accessible amino acid residues reactive with a pregabalin derivative having an appropriate reactive functional group.

Moieties of Interest of Pregabalin Conjugates

In certain embodiments, the moiety of interest of pregabalin conjugates of the present disclosure can be any suitable chemical entity or support, such as one adapted for use in an assay, or for generating reagents useful in such assays (e.g., anti-pregabalin antibody production), described herein.

Accordingly, in some instances, the moiety of interest can be, for example, an immunogenic carrier, a detectable label, or a support.

Examples of immunogenic carriers include, but are not limited to, polypeptides (which term is used to encompass amino acid chains of any length, including peptides and proteins), modified polypeptides (e.g., post-translationally and/or chemically modified, e.g., lipoproteins, glycoproteins, and the like), and polysaccharides. In certain embodiments, the immunogenic carrier is a polypeptide immunogenic carrier.

Further examples of moieties of interest include detectable labels, such as, but not limited to, polypeptides having an immunodetectable epitope (e.g., detectable by binding of a binding partner that specifically binds the epitope (e.g., an HA tag)), nucleic acids (which can be detectable by use of a hybridization probe or by PCR-based methods), radioactive isotopes, enzymes (including enzyme fragments, enzyme donor fragments, enzyme acceptor fragments, coenzymes), enzyme ligands (e.g., enzyme substrates, enzyme inhibitors), fluorescent moieties (including fluorophores and quenchers), phosphorescent moieties, anti-stokes up-regulating moieties, chemiluminescent moieties, luminescent moieties, chromophores, radioactive isotopes, and combinations thereof.

Further examples of moieties of interest include a support, such as, but not limited to, solid supports (e.g., arrays), particles (including gold particles, microparticles, magnetic particles, beads, and the like), and liposomes, and combinations thereof.

As described above, a "detectable label" generally refers to an identifying tag that can provide for a detectable signal, e.g., luminescence (e.g., photoluminescence (e.g., fluorescence, phosphorescence), chemoluminescence (e.g., bioluminescence)), radioactivity, immunodetection, enzymatic activity, and the like). Examples of a label include a polypeptide such as an antigen, enzyme, an antibody, a nucleic acid, a fluorophor, a quencher (e.g., of a FRET pair), a phosphorescent group, a chemiluminescent group, a chromophoric group, an electrochemically active group, an electrochemiluminescent group, a group that undergoes a change in fluorescence, phosphorescence, chemiluminescence or electrochemical property upon binding (e.g., as described in U.S. Pat. Nos. 6,203,974 and 6,159,750), a solid particle, a gold particle, a radioactive isotope, an enzyme ligand (e.g., an enzyme inhibitor, an enzyme substrate), an enzyme cofactor, a member of an enzyme donor-acceptor pair, and the like.

The detectable label can be a non-isotopic signal-generating moiety." "Non-isotopic signal-generating moiety", as used herein, refers to a moiety that does not emit radioactivity as a detectable signal. By way of example, a non-isotopic signal-generating moiety is an enzyme, fluorescent compound, or a luminescent compound.

Other examples of moieties of interest are further described below.

Pregabalin-Carrier Protein Conjugates

In some embodiments, the moiety of interest is an immunogenic carrier, such as an immunogenic carrier protein. Such pregabalin conjugates find use in production of anti-pregabalin antibodies, which in turn find use in the pregabalin detection assays described herein. Examples of carriers include, but are not limited to, proteins, glycoproteins, complex polysaccharides, particles, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Examples of proteins include bovine serum albumin (BSA), keyhole limpet hemocyanin (KLH), egg ovalbumin, bovine gamma-globulin (BGG), etc. Immunogenic polypeptides include genetically-encodable and synthetic polypeptides, and the like.

The immunogenic carrier can also be a polysaccharide, which includes high molecular weight polymers built up by repeated condensations of monosaccharides. Examples of polysaccharides are starches, glycogen, cellulose, carbohydrate gums such as gum arabic, agar, and so forth. The polysaccharide can also contain polyamino acid residues and/or lipid residues.

The immunogenic carrier can also be a poly(nucleic acid) either alone or conjugated to one of the above mentioned poly(amino acids) or polysaccharides. The immunogenic carrier can also be a particle. In certain embodiments, the particles are 0.01 microns or more in diameter, such as 0.01 micron to 100 micron, for example 0.05 micron to 10 micron in diameter. The particle can be organic or inorganic, swellable or non-swellable, porous or non-porous, optionally of a density approximating water, such as from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, Streptococcus, Staphylococcus aureus, E. coli, and viruses. The particles can also include organic and inorganic polymers, liposomes, latex, phospholipid vesicles, or lipoproteins, or combinations thereof.

Immunogenic carriers described herein include keyhole limpet hemocyanin (KLH) and bovine serum albumin (BSA). FIG. 5 and FIG. 6 show schematic representation of examples of pregabalin conjugates having a pregabalin moiety linked to KLH. Dimerized pregabalin conjugates can be linked through a disulfide bond, which may be reduced to generate monomeric pregabalin conjugates, e.g., by reaction with dithiothreitol (DTT) or tris(2-carboxyethyl)phosphine (TCEP). Pregabalin carrier protein conjugates may include a plurality of pregabalin derivatives covalently bonded to the protein carrier, as discussed in Formula (I'''), and Formula (II'''), above.

Pregabalin-Enzyme Conjugates

In certain embodiments, the moiety of interest of the pregabalin conjugate is an enzyme. In some instances, the enzyme can serve as a non-isotopic signal generating moiety, and may be any enzyme that provides for a detectable signal useful in, for example, an immunoassay described herein. Examples of enzymes include, but are not limited to, alkaline phosphatase, 3-galactosidase, horse radish peroxidase, glucose-6-phosphate dehydrogenase (G6PDH), and the like. The G6PDH refers to both a naturally occurring G6PDH and G6PDH variants that contain one or more cysteine residues non-native to naturally-occurring G6PDH (e.g., recombinant G6PDH, rG6PDH).

In some embodiments, pregabalin enzyme conjugates provide an immunoassay reagent that competes with pregabalin that may be present in a sample for binding to an anti-pregabalin antibody, where the presence or absence of a detectable signal provided by the enzyme is indicative of the presence or absence of a pregabalin-anti-pregabalin antibody complex. Pregabalin enzyme conjugates containing G6PDH (including naturally occurring G6PDH and G6PDH variants, such as G6PDH cysteine variants) find use in such assays.

FIG. 7, FIG. 8 and FIG. 9 show schematic representations of examples of pregabalin-enzyme conjugates, such as pregabalin rG6PDH, and G6PDH conjugates. Dimerized pregabalin-enzyme conjugates can be linked through a disulfide bond, which may be reduced to generate monomeric pregabalin enzyme conjugates, e.g., by reaction with DTT or TCEP. Pregabalin enzyme conjugates may include a plurality of pregabalin derivatives covalently bonded to the protein carrier, as discussed in Formulae (I'''), and (II''') above.

Other Pregabalin Conjugates

The moiety of interest may be a support, thus immobilizing the pregabalin conjugate. The moiety of interest may provide a detectable signal, such as a fluorophore, a fluorescence quencher, a radioisotope, and metal particle (e.g., in SERS-based assays). Pregabalin conjugates can include, for example, a first member of a FRET pair (e.g., a member of a fluorophore/quencher pair), where the pregabalin conjugate is used in connection with an anti-pregabalin antibody having the second member of the FRET pair, such that binding of the labeled anti-pregabalin antibody to the labeled pregabalin conjugate in a complex provides for a detectable signal different from that when the labeled anti-pregabalin antibody and labeled pregabalin conjugate are not in a complex with one another (e.g., as when binding of pregabalin blocks binding of the antibody to the pregabalin conjugate).

Methods of Making Pregabalin Conjugates

In certain embodiments, pregabalin conjugates are prepared by synthesizing a pregabalin derivative having a reactive functional group (e.g., as described above), and reacting the pregabalin derivative with a reactive partner (e.g., a protein) under conditions that permit a conjugation reaction to occur, and then isolating the conjugate from the reaction mixture.

For example, a protein conjugate can be prepared by combining an excess of a bromoacetyl adduct with a protein having one or more free thiol groups as described in U.S. Pat. No. 6,455,288, the disclosure of which is incorporated herein by reference. Free sulfhydryl groups may be provided in the form of free cysteine residues or by reducing protein disulfide bonds using a reducing reagent, such as dithiothreitol (DTT). Alternatively, thiol groups can be added to a protein having free primary amino groups by reacting with 2-iminothiolane (IT) in aqueous buffer, followed by removal of unreacted IT. Examples of protocols for the thiolation of the protein KLH are provided in U.S. Pat. No. 5,439,798, the disclosure of which is incorporated herein by reference. Other examples of methods of protein conjugation methods are further described in U.S. Pat. Nos. 6,033,890, 6,090,567, and 6,455,288, the disclosures of each of which are incorporated herein by reference.

Figure 3:
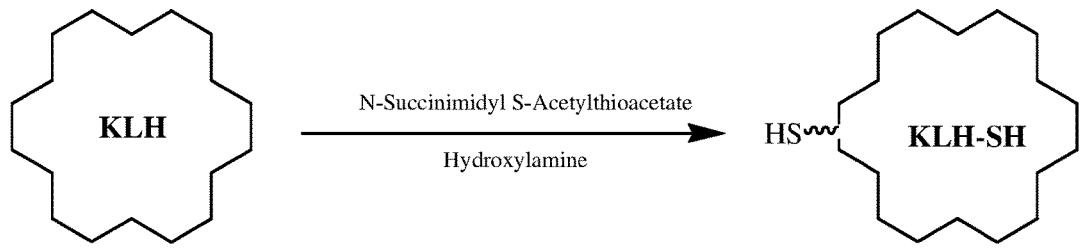
FIG. 3 is a schematic representation of the reparation of KLH-SH, according to embodiments of the present disclosure.
Figure 4:
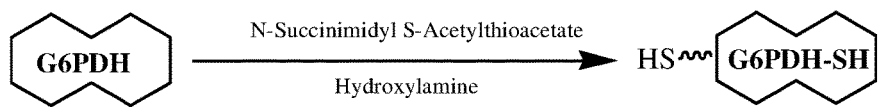
FIG. 4 is a schematic representation of preparation of wild type G6PDH-SH, according to embodiments of the present disclosure.

FIG. 3 and FIG. 4 show examples of thiolation of KLH and native G6PDH, respectively.

FIG. 5, FIG. 6, FIG. 7, FIG. 8 and FIG. 9 are schematic representations of synthesis schemes of examples of pregabalin-enzyme conjugates (e.g., rG6PDH and native G6PDH conjugates), and pregabalin-immunogenic carrier conjugates using KLH.

Anti-Pregabalin Antibodies

As noted above, the term "antibody" as used in the context of the present disclosure, refers to a specific binding partner of an analyte (e.g., pregabalin), and is meant to encompass whole antibodies as well as antigen-binding fragments thereof (such as, for example, F(ab')$_2$, Fab', Fab and Fv), naturally occurring antibodies, hybrid antibodies, chimeric antibodies, single-chain antibodies, and antibody fragments that retain antigen binding specificity, and the like.

Antibodies can be of any class (e.g., IgM, IgG, IgA, IgE; frequently IgG) and generated from any source (although usually non-human, usually a non-human mammal such as a rabbit, mouse, rat, goat, etc.). Thus, "antibody" is meant to encompass not only intact immunoglobulin molecules, but also such fragments and derivatives of immunoglobulin molecules as may be prepared by techniques known in the art, and retaining the antibody activity of an intact immunoglobulin.

Antibodies may be derived from polyclonal compositions or monoclonal compositions. As noted above, "antibodies" is also meant to encompass single chain antibodies or scFvs, where such recombinantly produced antibody fragments retain the binding characteristics of the above antibodies. Recombinantly produced antibody fragments within the meaning of "antibody" generally include at least the VH and VL domains of the subject antibodies, so as to retain the binding characteristics of the subject antibodies. These recombinantly produced antibody fragments may be readily prepared using any convenient methodology, such as the methodology disclosed in U.S. Pat. Nos. 5,851,829 and 5,965,371, the disclosures of which are herein incorporated by reference.

Anti-pregabalin antibodies include those that bind one or more pregabalin epitopes. Anti-pregabalin antibodies thus include antibodies that bind, particularly that specifically bind, one or more of an amine epitope of a pregabalin moiety, a carboxylic acid epitope of a pregabalin moiety, or any combination thereof (e.g., both an amine epitope and a carboxylic acid epitope). Anti-pregabalin antibodies may bind one or more of unconjugated pregabalin, a pregabalin derivative, a pregabalin conjugate, or any combination thereof.

Producing Anti-Pregabalin Antibodies

Anti-pregabalin antibodies can be prepared by using an immunogenic pregabalin conjugate described herein and applying methods for antibody production that are known in the art. For examples of general techniques used in raising, purifying and modifying antibodies, and the design and execution of immunoassays, the reader is referred to Handbook of Experimental Immunology (D. M. Weir & C. C. Blackwell, eds.); Current Protocols in Immunology (J. E. Coligan et al., eds., 1991); David Wild, ed., The Immunoassay Handbook (Stockton Press N.Y., 1994); and R. Masseyeff, W. H. Albert, and N. A. Staines, eds., Methods of Immunological Analysis (Weinheim: VCH Verlags gesellschaft mbH, 1993).

Antibodies obtained using any of the disclosed techniques are screened or purified not only for their ability to react with pregabalin, but for a low cross-reactivity with potential interfering substances. "Cross-reactivity" may be determined in a quantitative immunoassay by establishing a standard curve using known dilutions of the target analyte, pregabalin. The standard curve is then used to calculate the apparent concentration of the interfering substance present in various known amounts in samples assayed under similar condition. The cross-reactivity is the apparent concentration divided by the actual concentration multiplied by 100. An exemplary immunoassay for determining cross-reactivity is a homogeneous enzyme immunoassay using a wild type G6PDH as described in U.S. Pat. No. 3,817,837 or mutant G6PDH engineered to contain a cysteine per subunit as described in U.S. Pat. Nos. 6,033,890, 6,090,567 and 6,455, 288. Furthermore, the cross-reactivity can be determined in the same type of immunoassay in which the antibody will ultimately be used.

In certain embodiments, the subject immunoassays (e.g., the subject anti-pregabalin antibodies) have a crossreactivity for interfering substances (e.g., crossreactants), such as gabapentin, or amino acids (e.g., leucine), that is 10% or less, or 5% or less, or 1% or less, or 0.5% or less, or 0.1% or less, or 0.05% or less, or 0.01% or less, or 0.005% or less, or 0.001% or less.

Producing Polyclonal Antibodies

Polyclonal antibodies that bind pregabalin may be raised by administration of an immunogenic pregabalin conjugate to an animal host, usually mixed with an adjuvant. Any animal host which produces antibodies can be used. The immunogen may be prepared for injection by rehydrating lyophilized immunogen to form a solution or suspension. Examples of adjuvants include water-in-oil immersions, such as Freund's complete adjuvant for the first administration, and Freund's incomplete adjuvant for booster doses.

The preparation is typically administered in a variety of sites, and typically in two or more doses over a course of at least 4 weeks. Serum is harvested and tested for the presence of anti-pregabalin antibody using a pregabalin-protein conjugate or other pregabalin conjugates in a standard immunoassay or precipitation reaction.

Polyclonal antisera typically contain antibodies not reactive with pregabalin and cross-reactive with other substances. Methods for purifying specific antibodies from a polyclonal antiserum are known in the art. An example of a method is affinity purification using a column of pregabalin conjugated to a solid phase. One manner of preparing a pregabalin column is to conjugate pregabalin or a pregabalin derivative to a protein other than the protein used in the immunogen, and then attach the conjugate to a commercially available activated resin, such as CNBr-activated SEPHAROSE™. The anti-pregabalin antibody is passed over the column, the column is washed, and the antibody is eluted with a mild denaturing buffer such as 0.1 M glycine, 0.2 M NaCl, pH 2.5.

Producing Monoclonal Antibodies

Anti-pregabalin monoclonal antibodies may be prepared by a number of different techniques. For example, for hybridoma technology, techniques for producing monoclonal antibodies are described in Harrow E, Lane D., 1988, *Antibodies, A Laboratory Manual*, Cold Spring Harbor, N.Y.: Cold Spring Harbor Laboratory Press, U.S. Pat. Nos. 4,491,632, 4,472,500, and 4,444,887, and Methods in Enzymology, 73B:3 (1981). In certain embodiments, monoclonal antibodies are produced by immortalizing and cloning a splenocyte or other antibody-producing cell recovered from an animal that has been immunized against pregabalin as described earlier. The clone may be immortalized by a procedure such as fusion with a non-producing myeloma, by transfecting with Epstein Barr Virus, or transforming with oncogenic DNA. The treated cells may be cloned and cultured, and clones may be selected that produce antibody of the desired specificity. Specificity testing may be performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using biochemical preparation techniques, such as, but not limited to, ammonium sulfate precipitation, ion exchange chromatography, and gel filtration chromatography.

Producing Fragments and Other Derivatives of Immunoglobulins

Fragments and other derivatives of immunoglobulins can be prepared by methods of standard protein chemistry, for example, subjecting the antibody to cleavage with a proteolytic enzyme such as pepsin, papain, or trypsin; and reducing disulfide bonds with such reagents as dithiothreitol. Genetically, engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Detectably Labeled Anti-Pregabalin Antibodies

The anti-pregabalin antibodies may also be labeled in order to facilitate detection. A variety of protein labeling schemes may be employed as desired depending on the intended use of the antibody, e.g., immunoassay.

Examples of labels include labels that permit both the direct and indirect measurement of the presence of the antibody. Examples of labels that permit direct measurement of the antibody include radiolabels, such as $^3H$ or $^{125}I$, fluorescent labels, dyes, microparticles, beads, chemiluminescent labels, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g., the antibody may be covalently bound to biotin and the enzyme conjugate to streptavidin. Examples of suitable enzymes for use in conjugates include horseradish peroxidase, alkaline phosphatase, malate dehydrogenase and the like.

Immunoassays

The present disclosure provides immunoassay methods for assessing the presence or absence of pregabalin in a sample of interest. Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competition assays. The immunoassays may embody assays that are neither sandwich nor competition assays, as in certain assays involving immunoprecipitation.

In certain embodiments, the immunoassays of the present disclosure for detecting the presence of absence of pregabalin in a sample can be conducted by adding, to a reaction mixture, (i) a sample suspected of containing pregabalin and (ii) an anti-pregabalin antibody capable of forming of a complex with pregabalin that may be present in the sample; and detecting the presence or absence of the complex. The presence or absence of the complex is indicative of the presence or absence of pregabalin in the sample. Moreover, the amount of complex formed can be assessed to determine the concentration of pregabalin present in the sample (e.g., to provide an assessment of serum or tissue concentration of pregabalin in a subject from whom the sample was obtained). The presence and/or amount of complex can be assessed directly (e.g., by detecting bound antibody in the complex) or indirectly (e.g., by assessing activity of an enzyme in a pregabalin enzyme conjugate, where when the pregabalin enzyme conjugate is not bound to antibody, a detectable signal is generated, indicating that the anti-pregabalin antibody in the reaction mixture has been bound by pregabalin from the sample).

In some embodiments, the immunoassays of the disclosure include combining the sample with an anti-pregabalin antibody under conditions that permit the formation of a stable complex between the analyte to be tested (e.g., pregabalin) and the antibody.

Assays may be performed in solution or may use a solid (insoluble) support (e.g. polystyrene, nitrocellulose, or beads), using any standard methods (e.g., as described in Current Protocols in Immunology, Coligan et al., ed.; John Wiley & Sons, New York, 1992). Such methods include ELISAs (enzyme-linked immunosorbent assays), IRMAs (immunoradiometric assays), and RIAs (radioimmunoassays).

Where the assay is performed in solution, the test samples (and, optionally a control sample) may be incubated with an anti-pregabalin antibody for a time period sufficient to allow formation of analyte and affinity reagent complexes, for example, from 1 min to 24 hrs, or more. As previously noted, the anti-pregabalin antibody may include a detectable label (e.g., radionuclide, fluorescer, or enzyme). The sample may then be treated to separate the pregabalin-anti-pregabalin antibody complexes from excess, unreacted anti-pregabalin antibody (e.g., by addition of an anti-anti-pregabalin antibody (e.g., anti-immunoglobulin antiserum) followed by centrifugation to precipitate the complexes, or by binding to an affinity surface such as a second, unlabeled anti-pregabalin antibody fixed to a solid substrate (such as Sepharose® or a plastic well). Detection of anti-pregabalin antibody bound to a pregabalin may be achieved in a variety of ways. For example, if necessary, a substrate for the detectable label may be added to the sample.

Where the assay uses a solid support, the support can have an anti-pregabalin antibody (or pregabalin conjugate) bound to a support surface. Binding of the assay reagent may facilitate the stable, wash-resistant binding of pregabalin, which may be present in the sample (or anti-pregabalin antibody that is not bound to pregabalin from the sample, and is present in the reaction mixture, as in a competitive binding assay) to the solid support via specific binding to the anti-pregabalin antibody. The insoluble supports may be any composition to which antibodies or suitable pregabalin conjugates can be bound, which is readily separated from soluble material, and which is otherwise compatible with the overall method of detection of anti-pregabalin antibody a sample.

The surface of such supports may be solid or porous and of any convenient shape. Examples of suitable insoluble supports to which the anti-pregabalin antibody can be bound include beads, e.g. magnetic beads, membranes and microtiter plates. These can be composed of glass, plastic (e.g. polystyrene), polysaccharides, nylon or nitrocellulose.

Assay reagents can include the anti-pregabalin antibodies as disclosed herein, as well as anti-anti-pregabalin antibodies, which may be optionally detectably labeled. Methods for binding antibodies or other proteins to solid supports may be used. After binding of an assay reagent to the support, the support may be treated with a blocking agent, which binds to the support in areas not occupied by the assay reagent. Suitable blocking agents include non-interfering proteins such as bovine serum albumin, casein, gelatin, and the like. Alternatively, detergents at non-interfering concentrations, such as Tween, NP40, TX100, and the like may be used. Such blocking treatment may reduce nonspecific binding.

Qualitative and Quantitative Methods

Assays of the present disclosure include both qualitative and quantitative assays. Typical quantitative methods involve mixing an analyte with a pre-determined amount of the reagent antibody, and correlating the amount of complex formed with the amount of analyte in the original sample. In some embodiments, the correlation is based on a relationship determined using standard samples containing known amounts of analyte in the range expected for the sample to be tested. In a qualitative assay, sufficient complex above or below a threshold level established by samples known to contain or be free of analyte establish the assay result.

Unless otherwise stated, the act of "measuring" or "determining" in this disclosure refers to both qualitative and quantitative determination.

Samples

Samples may be biological samples taken from subjects suspected of being administered the analyte, e.g., pregabalin.

A sample suspected of containing or containing analyte refers to any sample which is reasonably suspected of containing analyte that can be analyzed by the methods of the present disclosure. Such samples can include human, animal or man-made samples. The sample can be prepared in any convenient medium which does not interfere with the assay. Typically, the sample is an aqueous solution or a natural fluid, such as, urine, whole blood, serum, plasma, cerebral-spinal fluid, or saliva. In some instances, the sample is serum or hair.

As used herein, a "sample" refers to a sample of tissue or fluid isolated from a subject, which in the context of the present disclosure generally refers to samples suspected of containing pregabalin, which samples, after optional processing, can be analyzed in an in vitro assay.

Examples of samples of interest include, but are not limited to, a "blood sample" (which as used herein is meant to include whole blood, plasma, serum, and the like), fecal matter, urine, tears, sweat saliva, milk, organs, biopsies, secretions of the intestinal and respiratory tracts, vitreous humor, and fluids obtainable during autopsy (such as cerebrospinal fluid). A "blood-derived sample" refers to a sample that is prepared from blood or a fraction thereof, e.g., plasma or serum. Respiratory secretions (e.g., samples obtained from fluids or tissue of nasal passages, lung, and the like), "Human serum", as used herein, refers to the aqueous portion of human blood remaining after the fibrin and suspended material (such as cells) have been depleted.

Blood samples, such as serum samples, can be obtained by any suitable method. In some embodiments, a trough serum/plasma is used and the concentration range is 12-20 mg. Sweat samples can be obtained using, for example, a PharmChek® sweat patch from Sudormed. The PharmChek® sweat patch includes a semi-occlusive dressing containing a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) or with acetonitrile. Furthermore, the biological samples may also be tissue samples, which are extracted into liquid medium for immunoassay. For example, hair samples can be tested by extracting into a liquid medium. The samples may be diluted or modified to facilitate the assay.

The samples may be experimental samples generated by any chemical or biological method. For example, the samples may be standards containing known concentrations of pregabalin or other substances used for assay calibration.

In some embodiments, the biological sample may be diluted in a suitable solution prior to assaying. In some embodiments, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

Where desired, appropriate control samples for the assay include blood, serum, or urine collected from human subjects who have not received pregabalin (i.e., a negative control), or samples which contain a known, predetermined amount of a pregabalin analyte (i.e., a positive control). Alternatively, test results can be compared to detectable signal levels known to be associated with the presence or absence of pregabalin and/or correlated with an amount of pregabalin, e.g., a serum level of pregabalin.

The assays may optionally include use of a calibration standard. "Calibration standard", as used herein, refers to an aqueous medium containing pregabalin at a predetermined concentration. In some embodiments, a series of these calibration standards are available at a series of predetermined concentrations. In some embodiments, the calibration standard is stable at ambient temperature. In some embodiments, the calibration standards are in a synthetic matrix. In some embodiments, the calibration standards are in a non-synthetic matrix such as human serum.

In some embodiments, a suitable initial source for the human sample is a blood sample. As such, the sample employed in the subject assays is generally a blood-derived sample. The blood derived sample may be derived from whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In some embodiments, the method employs drawing venous blood by skin puncture (e.g., finger stick, venipuncture) into a clotting or serum separator tube, allowing the blood to clot, and centrifuging the serum away from the clotted blood. The serum may then be collected and stored until assayed. Once the patient derived sample is obtained, the sample may be assayed to determine the level of pregabalin analyte.

Immunoassay Reagents

Immunoassay reagents that find use alone or in combination in the assays described herein include anti-pregabalin antibodies, pregabalin conjugates, and pregabalin (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives are introduced to maintain hydrophobic or low-solubility compounds in solution, and stabilize components in the solution. Examples include bulking agents such as betalactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

Anti-Pregabalin Antibodies

Immunoassays generally involve at least one anti-pregabalin antibody, which may be produced by the methods disclosed herein. In some embodiments, the assays involve using an antibody raised against a pregabalin derivative-protein conjugate, such as an antibody having a low cross-reactivity with non-pregabalin molecules that may be present in a reaction mixture. Anti-pregabalin antibodies can be polyclonal or monoclonal antibodies, capable of specifically binding pregabalin.

Depending upon the assay format, the anti-pregabalin antibody can be optionally detectably labeled, may be used in conjunction with a secondary antibody (e.g., an antibody that specifically binds an anti-pregabalin antibody) that may be detectably labeled. Examples of detectable labels for antibodies are described herein.

Pregabalin Conjugates

Pregabalin conjugates of the present disclosure find use as immunoassay reagents depending on the assay format. For example, a pregabalin conjugate can act as a competitive binding reagent in competitive binding assays, or can provide for a detectable signal when not bound by an anti-pregabalin antibody (e.g., where the pregabalin conjugate is a pregabalin G6PDH conjugate). Examples of pregabalin conjugates useful as immunoassay reagents are described below.

Detectable Labels

A variety of detectable labels can be used in connection with the pregabalin conjugate assay reagents for use in the methods disclosed herein. Such detectable labels can be isotopic labels. In other embodiments, the detectable labels are non-isotopic signal-generating moieties, such as fluorophores and enzymes. Exemplary detectable labels are described below. It will be apparent that while the detectable labels are described below in the context of their use in pregabalin conjugates, many can also be adapted for use with anti-pregabalin antibodies.

Fluorophores

"Fluorophore" as used herein refers to a moiety that itself fluoresces, can be made to fluoresce, or can provide for quenching of fluorescence of a fluorophor of a FRET pair (e.g., as in a FRET pair). In principle, any fluorophore can be used in the assays of this invention. In general, the fluorophore is selected so as to be compatible for use in the assay format desired, and selected so as to be relatively insensitive to the assay conditions, e.g., pH, polarity, temperature and ionic strength.

Examples of fluorophores can be characterized as having one or more of the following characteristics: (a) A fluorescence lifetime of greater than about 15 nsec; (b) An excitation wavelength of greater than about 350 nm; (c) A Stokes shift (a shift to lower wave-length of the emission relative to absorption) of greater than about 20 nm; (d) For homogeneous assays described below, fluorescence lifetime should vary with binding status; and (e) The absorptivity and quantum yield of the fluorophore should be high. The longer lifetime may be advantageous because it may facilitate measurement and may be more easily distinguishable from the Raleigh scattering (background). Excitation wavelengths greater than 350 nm may facilitate a reduction in background interference because most fluorescent substances responsible for background fluorescence in biological samples are excited below 350 nm. A greater Stokes shift may also allow for less background interference.

The fluorophores generally have a functional group available for conjugation either directly or indirectly to a pregabalin intermediate to generate a pregabalin conjugate having the attached fluorophore.

Fluorophores for use in heterogenous assays can be relatively insensitive to binding status. In contrast, fluorophores for use in homogeneous assay can be sensitive to binding status, i.e., the fluorescence lifetime may be alterable by binding so that bound and free forms can be distinguished.

Examples of fluorophores useful in the present disclosure include, but are not limited to, naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Enzymes

In some embodiments, the signal-generating moiety is an enzyme. The enzyme can be selected so as to be stable to provide for desirable shelf-life, e.g., stable when stored for a period of three months or more, or six months or more, at temperatures which are convenient to store in the laboratory, normally −20° C., or above. The enzyme can be selected so as to have a satisfactory turnover rate at or near the pH optimum for binding to the antibody, such as at about pH 6-10, or for example from pH 6.0 to pH 8.0. A product of the enzymatic reaction facilitated by the enzyme can be either formed or destroyed as a result of the enzyme reaction, and can provide an enzyme reaction product which absorbs light in the ultraviolet region or the visible region, such as a wavelength range of about 250-750 nm, for example from 300-600 nm. The enzyme may also have a substrate (including cofactors) which has a molecular weight of 300 Da or more, or 500 Da or more. The enzyme which is employed or other enzymes, with like activity, may not be present in the sample to be measured, or can be easily removed or deactivated prior to the addition of the assay reagents. Also, the enzyme can be selected so as to avoid the impact of any naturally occurring inhibitors for the enzyme that may be present in samples to be assayed or as some other component of the reaction mixture.

Although enzymes of up to 600,000 molecular weight can be employed, in some embodiments, relatively low molecular weight enzymes will be employed of from 10,000 to 300,000 molecular weight, such as from 10,000 to 150,000 molecular weight, or from 10,000 to 100,000 molecular weight. Where an enzyme has a plurality of subunits the molecular weight refers to the enzyme and not to the subunits.

It may be desirable to select an enzyme that is susceptible to detectable labeling. In this instance, the enzyme can be detectable labeled using appropriate detectable labels described herein.

Examples of enzymes include, but are not limited to: alkaline phosphatase, horseradish peroxidase, lysozyme, glucose-6-phosphate dehydrogenase, lactate dehydrogenase, β-galactosidase, and urease. A genetically engineered fragment of an enzyme may be used, such as the donor and acceptor fragment of β-galactosidase utilized in CEDIA immunoassays (see, e.g., Henderson D R et al. *Clin Chem.* 32(9):1637-1641 (1986)); U.S. Pat. No. 4,708,929. These and other enzymes which can be used are described by Eva Engvall in Enzyme Immunoassay ELISA and EMIT in Methods in Enzymology, 70:419-439 (1980) and in U.S. Pat. No. 4,857,453.

In some embodiments, the enzyme is glucose-6-phosphate dehydrogenase (G6PDH) and it is attached to a pregabalin derivative, thus forming a pregabalin-reactive partner conjugate. An anti-pregabalin antibody used in conjunction with such pregabalin conjugates can be selected so as to specifically bind the pregabalin epitope presented by the pregabalin enzyme conjugate, and thus affect activity of the pregabalin enzyme conjugate.

For assays employing pregabalin-enzyme conjugates, as an example of a protein conjugate, in which a hapten is labeled with an enzyme, the hapten can be attached to the enzyme by any suitable method. In certain embodiments, the chemistry described herein for formation of immunogenic protein conjugates of pregabalin derivatives is also used to prepare the enzyme conjugate. In this way, the pregabalin moiety presented to the antibody can be similar to the pregabalin epitope to which the antibody specifically binds.

The selection procedure may include the use of a hapten-reactive partner conjugate including G6PDH as the reactive partner and a pregabalin derivative as the hapten. The first step in selecting an antibody may include testing the magnitude of antibody inhibition of a hapten-reactive partner conjugate. In this step, the goal is to determine and select for those antibodies which significantly inhibit the enzyme activity of G6PDH. Antibodies which perform well in the first test may then be subjected to a second test. Here, the antibody is first incubated with pregabalin. Next the hapten-reactive partner conjugate is added. An subject antibody preferentially binds to pregabalin instead of the pregabalin-reactive partner conjugate. The reduction in binding to the hapten-reactive partner conjugate would be detectable as an increase G6PDH activity.

Detection

Via Fluorescence

In certain embodiments, when a fluorescently labeled analyte (i.e., pregabalin antigen or antibody) is employed, the fluorescence emitted is proportional (either directly or inversely) to the amount of analyte. The amount of fluorescence can be determined by the amplitude of the fluorescence decay curve for the fluorescent species. In some instances, this amplitude parameter is directly proportional to the amount of fluorescent species, and accordingly to the analyte.

In some cases, spectroscopic measurement of fluorescence is accomplished by: (a) exciting the fluorophore with a pulse of light; (b) detecting and storing an image of the excitation pulse and an image of all the fluorescence (the fluorescent transient) induced by the excitation pulse; (c) digitizing the image; (d) calculating the true fluorescent transient from the digitized data; and (e) determining the amplitude of the fluorescent transient as an indication of the amount of fluorescent species.

According to the method, substantially all of the fluorescence emitted by the fluorescent species reaching the detector as a function of time from the instant of excitation is measured. As a consequence, the signal being detected is a superimposition of several component signals (for example, background and one analyte specific signal). As mentioned, the individual contributions to the overall fluorescence reaching the detector can be distinguished based on the different fluorescence decay rates (lifetimes) of signal components. In order to quantitate the magnitude of each contribution, the detected signal data can be processed to obtain the amplitude of each component. In some instances, the amplitude of each component signal is proportional to the concentration of the fluorescent species.

Via Enzyme

Detection of the amount of product produced by the hapten-reactive partner conjugate of the invention can be accomplished by several methods. Among these methods are colorimetry, fluorescence, and spectrophotometry. These methods of detection are discussed in "Analytical Biochemistry" by David Holme, Addison-Wesley, 1998, which is incorporated herein by reference.

Solid Supports

The pregabalin conjugates and/or the anti-pregabalin antibodies to be used as reagents in an assay can be insolubilized by attachment to a solid phase. This can be, for example, a wall of a vessel containing the reagent, to a particulate, or to a large molecular weight carrier that can be kept in suspension but is removable by physicochemical means, such as centrifugation or microfiltration. The attachment need not be covalent, but is at least of sufficient permanence to withstand the separation techniques (including washes) that may be part of the assay procedure. Examples of particulate materials include, but are not limited to, agarose, polystyrene, cellulose, polyacrylamide, latex particles, magnetic particles, and fixed red cells. Examples of commercially available matrices include Sepharose® (Pharmacia), Poros® resins (Roche Molecular Biochemicals), Actigel Superflow™ resins (Sterogene Bioseparations Inc.), and Dynabeads™ (Dynal Inc.). In some instances, the support used depends on such features as stability, capacity, accessibility of the coupled antibody, flow rate (or the ability to disperse the resin in the reaction mixture), and ease of separation.

Assay Formats

As noted above, immunoassays for detection of pregabalin can be of a variety of formats. In certain embodiments, the immunoassays involve combining one or more immunoassay reagents (e.g., at least an anti-pregabalin antibody) with a test sample (e.g., a sample suspected of containing pregabalin) in a reaction mixture. "Reaction mixture" generally refers to the combination of a sample suspected of containing pregabalin and one or more immunoassay reagents as described in the present disclosure to facilitate detection of the presence or absence of pregabalin in the sample, where the detection may be qualitative or quantitative. The reaction mixture is usually an aqueous solution, although the immunoassay reagent(s) may be in solution or immobilized on a support (e.g., a substrate such as a bead). The reaction mixture can include other components compatible with the immunoassay, e.g., buffers, and the like.

Immunoassays usually are classified in one of several ways. For example, immunoassays can be classified according to the mode of detection used, e.g., enzyme immunoassays, radio immunoassays, fluorescence polarization immunoassays, chemiluminescence immunoassays, turbidimetric assays, etc. Another grouping is according to the assay procedure used, e.g., competitive assay formats, sandwich-type assay formats as well as assays based on precipitation or agglutination principles. In some cases, a further distinction is made depending on whether washing steps are included in the procedure (so-called heterogeneous assays) or whether reaction and detection are performed without a washing step (so-called homogeneous assays). Examples of assays are described in more detail below.

Homogeneous and Heterogeneous Immunoassays

Immunoassays may be described as heterogeneous or homogeneous. "Homogeneous immunoassay", as used herein, refers to an assay method where the complex is typically not separated from unreacted reaction components, but instead the presence of the complex is detected by a property which at least one of the reactants acquires or loses as a result of being incorporated into the complex. Homogeneous assays include systems involving fluorochrome and fluorochrome quenching pairs on different reagents, enzyme and enzyme inhibitor pairs on different reagents, chromophore and chromophore modifier pairs on different reagents, and latex agglutination assays, and the like.

An example of a homogeneous assay is the quantitative homogeneous enzyme immunoassay in which a pregabalin moiety is conjugated to an active enzyme. In some instances, the conjugation is arranged so that the binding of an anti-pregabalin antibody to the derivative affects enzymatic activity in a qualitative or quantitative fashion. For example, if a sample containing pregabalin is premixed with the antibody, the antibody will complex with the pregabalin and be prevented from binding to the enzyme conjugate. In this way, the activity of the enzyme can be correlated with the amount of pregabalin present in the sample.

G6PDH is an example of an enzyme useful in such assays. In some embodiments, the G6PDH is a variant of a naturally-occurring G6PDH in which one or more lysine residues are deleted or substituted, or one or more cysteine residues are introduced. For example, *Leuconostoc mesenteroides* G6PDH are dimeric enzymes that have the ability to catalyze the oxidation of D-glucose-6-phosphate to D-glucono-delta-lactone-6-phosphate by utilizing either $NAD^+$ or $NADP^+$. This property of using $NAD^+$ differentiates these enzymes from human G6PDH, which utilizes only $NADP^+$ effectively, and allows *L. mesenteroides*-specific G6PDH activity to be measured in the presence of human G6PDH, as for example in human samples. In some embodiments, G6PDHs from *L. mesenteroides* are used in homogeneous immunoassays. Two examples of genera of bacteria from which to select G6PDH are *Leuconostoc* and *Zymomonas*. Within these genera *L. mesenteroides, L. citreum, L. lactis, L. dextranicum*, and *Z. mobilis* may be used. For example, *L. mesenteroides, L. citreum, L. lactis* are specific examples.

Figure 10:
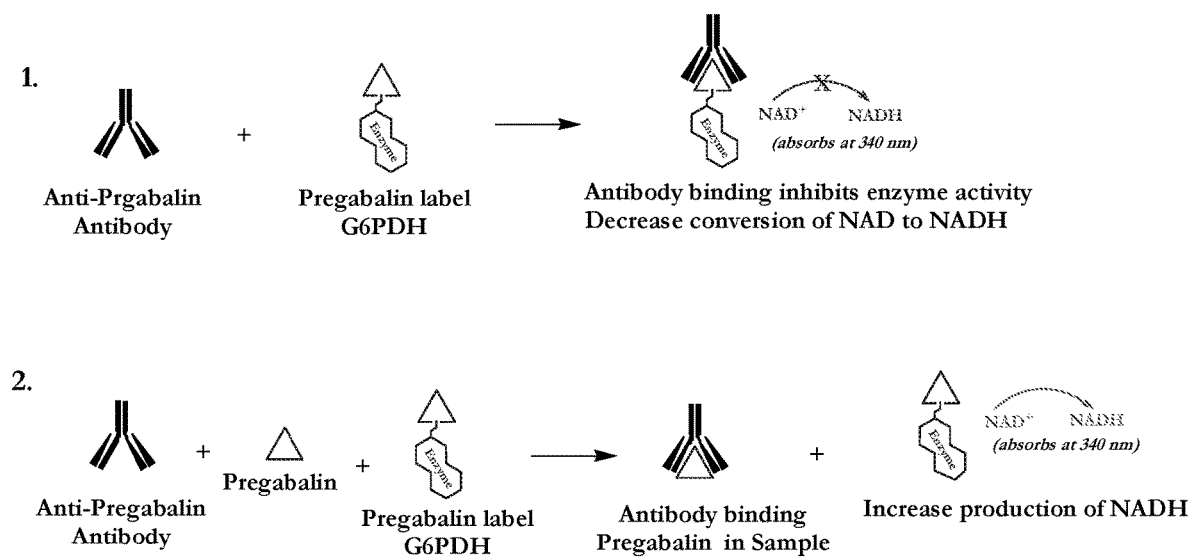
FIG. 10, panel 1, and FIG. 10, panel 2, show schematic representations of a homogeneous, competitive immunoassay for pregabalin using an anti-pregabalin antibody and a pregabalin-G6PDH enzyme conjugate according to embodiments of the present disclosure. As shown in reaction scheme 1 in FIG. 10, panel 1, in the absence of plasma drug (pregabalin), the anti-pregabalin antibody binds to the pregabalin-enzyme(G6PDH) conjugate and inactivates the enzyme. As shown in reaction scheme 2 in FIG. 10, panel 2, in the presence of plasma drug, pregabalin from plasma, if present, competes with the pregabalin-G6PDH conjugate for binding to the antibody, thus allowing some fraction of the pregabalin-G6PDH conjugate to become active and convert $NAD^+$ to NADH.

FIG. 10 shows a scheme of a homogeneous, competitive immunoassay for pregabalin using an anti-pregabalin antibody and a pregabalin-G6PDH enzyme conjugate in a sample (e.g., a plasma sample). As shown in reaction scheme 1 in FIG. 10, panel 1, in the absence of plasma drug (pregabalin), the anti-pregabalin antibody binds to the pregabalin-enzyme(G6PDH) conjugate and inactivates the enzyme. As shown in reaction scheme 2 in FIG. 10, panel 2, in the presence of plasma drug, pregabalin from plasma, if present, competes with the pregabalin-G6PDH conjugate for binding to the antibody, thus allowing some fraction of the pregabalin-G6PDH conjugate to become active and convert $NAD^+$ to NADH. The active G6PDH produces an absorbance signal change over time at 340 nm. In some instances, the analyte to be detected (pregabalin) is exposed to the antibody before the pregabalin-G6PDH conjugate to minimize saturation of the antibody with pregabalin-G6PDH conjugate. In these embodiments, the assay includes incubation of the sample and antibody before addition of the pregabalin-G6PDH conjugate.

Another example of a homogeneous assay system is a cloned enzyme donor immunoassay, described in more detail below.

In a separation-based or "heterogenous" assay, the detecting of a complex of an anti-pregabalin antibody and an analyte may include a process where the complex formed is physically separated from either unreacted analyte, unreacted antibody, or both.

In certain embodiments of a heterogenous immunoassay, a complex of an anti-pregabalin antibody and an analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or antibody to facilitate detection or quantitation of the complex.

Suitable labels include radioisotopes such as $^{125}I$, enzymes such as peroxidase and β-galactosidase, and fluorescent labels such as fluorescein isothiocyanate. In certain instances, the separation step includes removing labeled reagent present in complex form from unreacted labeled reagent. The amount of label in the complex can be measured directly or inferred from the amount left unreacted.

Sandwich and Competition Assays

Assays of the present disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with a derivative of the analyte for binding to another reagent, such as an antibody. An example of a competition assay using EMIT® is described in U.S. Pat. No. 3,817,837.

In some embodiments, the immunoassay includes adding a pregabalin conjugate having a pregabalin moiety and a detectable label to the sample. The presence or absence of pregabalin in the sample can be detected by detecting the detectable label. The detectable label may include an enzyme and the detecting may be performed by assaying the activity of the enzyme. In some embodiments, the enzyme is a dehydrogenase, such as G6PDH.

Lateral Flow Chromatography

Aspects of the present disclosure include lateral flow chromatography. In certain embodiments of lateral flow chromatography, a membrane strip that includes a detection device, such as a non-isotopic signal generating moiety, is used for detecting pregabalin. A sample from a patient can be applied to the membrane strip. The sample interacts with the detection device, producing a result. The results can signify several things, including the absence of pregabalin in the sample, the presence of pregabalin in the sample, and/or the concentration of pregabalin in the sample.

In certain embodiments, a method of qualitatively determining the presence or absence of pregabalin in a sample through the use of lateral flow chromatography is provided. In some embodiments, the qualitative lateral flow device includes: (1) A sample pad where the sample is applied. The sample pad may be treated with chemicals such as buffers or salts, which, when redissolved, facilitate reaction of the sample with the conjugate, test, and control reagents; (2) A conjugate release pad, such as a polyester or glass fiber material that is treated with a conjugate reagent such as an antibody colloidal gold conjugate. A typical process for treating a conjugate pad is to use impregnation followed by drying. In use, the liquid sample added to the test will redissolve the conjugate so that it will flow into the membrane; (3) The membrane substrate is usually made of nitrocellulose or a similar material whereby antibody capture components are immobilized; (4) A wicking pad can be used in tests where blood plasma is separated from whole blood. An impregnation process is usually used to treat this pad with reagents intended to condition the sample and promote cell separation; (5) An absorbent pad can provide a reservoir for collecting fluids that have flowed through the device; and (6) The above layers and membrane system can be laminated onto a plastic backing with adhesive material which serves as a structural member.

In certain embodiments, a method of qualitatively determining the presence of a pregabalin in a sample through the use of lateral flow chromatography is provided. In some embodiments, the membrane strip includes a sample pad, which is a conjugate release pad (CRP), which includes an antibody that is specific for the pregabalin. This antibody can be conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. The membrane strip may include a capture line, in which the pregabalin derivative antigen is immobilized on the strip. In some embodiments, this immobilization is through covalent attachment to the membrane strip, optionally through a linker. In other embodiments, the immobilization is through non-covalent attachment to the membrane strip. In still other embodiments, the immobile pregabalin derivative in the capture line is attached to a reactive partner, such as an immunogenic carrier like BSA.

Sample from a patient can be applied to the sample pad, where it can combine with the antibody in the CRP, thus forming a solution. This solution may then migrate chromatographically by capillary action across the membrane. When pregabalin is present in the sample, a pregabalin-antibody complex can be formed, which migrates across the membrane by capillary action.

When the solution reaches the capture line, the pregabalin-antibody complex may compete with the immobile pregabalin for the limited binding sites of the antibody. When a sufficient concentration of pregabalin is present in the sample, it may fill the limited antibody binding sites. This may prevent the formation of a colored antibody-immobile pregabalin complex in the capture line. Therefore, absence of color in the capture line indicates the presence of pregabalin in the sample.

In the absence of pregabalin in the sample, a colored antibody-immobile pregabalin complex can form once the solution reaches the capture line of the membrane strip. The formation of this complex in the capture line is evidence of the absence of pregabalin therapeutic in the sample.

In certain embodiments, a method of quantitatively determining the amount of a pregabalin in a sample through the use of lateral flow chromatography is provided. Lateral flow chromatography is further described in U.S. Pat. Nos. 4,391,904; 4,435,504; 4,959,324; 5,264,180; 5,340,539; and 5,416,000, which are herein incorporated by reference. In some embodiments, the antibody is immobilized along the entire length of the membrane strip. In certain cases, if the membrane strip is made from paper, the antibody is covalently bound to the membrane strip. In some cases, if the membrane strip is made from nitrocellulose, then the antibody can be non-covalently attached to the membrane strip through, for example, hydrophobic and electrostatic interactions.

In certain embodiments, the membrane strip includes a CRP, which includes the pregabalin attached to a detector moiety. In some embodiments, the detector moiety is an enzyme, such as horseradish peroxidase (HRP).

Sample from a patient can be applied to the membrane strip, where it can combine with the pregabalin/detector molecule in the CRP, thus forming a solution. This solution may then migrate chromatographically by capillary action across the membrane. When pregabalin is present in the sample, both the sample pregabalin and the pregabalin/detector molecule compete for the limited binding sites of the antibody. When a sufficient concentration of pregabalin is present in the sample, it may fill the limited antibody binding sites. This may cause the pregabalin/detector molecule to continue to migrate in the membrane strip. The shorter the distance of migration of the pregabalin/detector molecule in the membrane strip, the lower the concentration of pregabalin in the sample, and vice versa. When the pregabalin/detector molecule includes an enzyme, the length of migration of the pregabalin/detector molecule can be detected by applying an enzyme substrate to the membrane strip. Detection of the product of the enzyme reaction may then be utilized to determine the concentration of pregabalin in the sample.

In some embodiments, the enzyme's color producing substrate, such as a modified N,N-dimethylaniline, is immobilized to the membrane strip and 3-methyl-2-benzothiazolinone hydrazone is passively applied to the membrane, thus alleviating the need for a separate reagent to visualize the color producing reaction.

Fluorescence Polarization Immunoassay for Pregabalin

Fluorescence polarization immunoassay (FPIA) technology is based on competitive binding between an antigen/drug in a sample and a known concentration of labeled antigen/drug. FPIA technology is described in, for example, U.S. Pat. Nos. 4,593,089, 4,492,762, 4,668,640, and 4,751,190, which are incorporated herein by reference. Accordingly, the FPIA reagents, systems, and methods can be used with anti-pregabalin antibodies which are also anti-pregabalin analog antibodies.

The FPIA technology can be used to identify the presence of pregabalin and can be used in assays that quantify the amount of pregabalin in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled pregabalin or derivative thereof, which is small and rotates rapidly in solution, the emitted light is significantly depolarized. When the fluorescent-labeled pregabalin or derivative interacts with or is bound to an antibody, the rotation is slowed and the emitted light is highly polarized. This is because the antibody significantly and measurably increases the size of the complex. Also, increasing the amount of unlabeled pregabalin in the sample can result in decreased binding of the fluorescent-labeled pregabalin or derivative by the anti-pregabalin antibody, and thereby decrease the polarization of light emitted from sample. The quantitative relationship between polarization and concentration of the unlabeled pregabalin in the sample can be established by measuring the polarization values of calibrations with known concentrations of pregabalin. Thus, FPIA can be used to identify the presence and concentration of pregabalin in a sample.

In some embodiments, the assay involves an FPIA assay system. An example of components of the FPIA system can include the following: (i) monoclonal or polyclonal anti-pregabalin antibodies capable of specifically binding to pregabalin and a pregabalin derivative; (ii) a sample suspected of containing the pregabalin; and (iii) pregabalin derivative labeled with a fluorescent moiety, such as fluorescein. In some cases, the system can be provided as a kit exclusive of the sample. Additionally, the system or kit can include various buffer compositions, pregabalin concentration gradient compositions or a stock composition of pregabalin, and the like.

Homogeneous Microparticle Immunoassay for Pregabalin

Homogeneous microparticles immunoassays ("HMI"), which can be referred to as immunoturbidimetric assays, are based on the agglutination of particles and compounds in solution. When particles and/or chemical compounds agglutinate, particle sizes can increase and increase the turbidity of a solution. Accordingly, anti-pregabalin antibodies can be used with microparticles and pregabalin derivatives in order to assess the presence, and optionally the amount, of pregabalin in a sample. HMI technologies can be advantageous because the immunoassays can be performed on blood, blood hemolysate, serum, plasma, tissue, and/or other samples. HMI assays can be configured to be performed with pregabalin and/or a pregabalin derivative loaded onto a microparticle, or with an anti-pregabalin antibody loaded onto a microparticle. HMI or immunoturbidimetric assays can be used for measuring agglutination of substances in a sample.

Immunoturbidimetric assay technologies are described in, e.g., U.S. Pat. Nos. 5,571,728, 4,847,209, 6,514,770, and 6,248,597, which are incorporated herein by reference. Such assays involve light attenuation, nephelometric, or turbidimetric methods. The formation of an agglutinated compound (AB) from pregabalin (A) and anti-pregabalin antibody microparticle binding partner (B) can be measured by the change which occurs in the scattering or absorption of the incident light directed into the sample. In some embodiments, the anti-pregabalin antibody (A) can bind with a pregabalin or derivative loaded microparticle. When suspendable particles having an immobilized binding partner are used, there can be an enhancement of the effects, which makes it possible to determine low pregabalin concentrations. These homogeneous methods can be carried out quickly and simply, and permit the automation of sample analyses as described in more detail below.

Cloned Enzyme Donor Immunoassays for Pregabalin

Cloned enzyme donor Immunoassays ("CEDIA®", Roche Diagnostics), are based on the competition of pregabalin in the biological sample with a pregabalin conjugate containing an inactive genetically engineered enzyme-donor ("ED") fragment, such as from β-D-galactoside galactohydrolase or β-galactosidase ("β-gal") from $E.\ coli$, for binding to an antibody capable of binding pregabalin. If pregabalin is present in the sample, it binds to the antibody, leaving the ED portion of the ED-derivative conjugate free to restore enzyme activity of β-D-galactoside galactohydrolase or B gal in the reaction mixture so as to be capable of association with enzyme acceptor ("EA") fragments. The active enzyme that includes the ED and EA is then capable of producing a quantifiable reaction product when exposed to an appropriate substrate. An example of a substrate is chlorophenol red-β-D-galactopyranoside ("CPRG"), which can be cleaved by the active enzyme into galactose and CPR, where CPR can be measured by absorbency at about wavelength 570 nm. When pregabalin is not present in the sample, the antibody binds to the ED-derivative conjugate, thereby inhibiting association of the ED fragments with the EA fragments and inhibiting restoration of enzyme activity. In some cases, the amount of reaction product and resultant absorbance change are proportional to the amount of pregabalin in the sample.

Chemiluminescent Heterogeneous Immunoassays for Pregabalin

A competitive assay using chemiluminescent microparticle immunoassay ("CMIA") technology can also be used to assess whether or not pregabalin is present in a sample. Various types of CMIA heterogeneous immunoassays can be used for determining the presence and/or amount of a chemical entity in a sample. CMIA assays can include the use of anti-pregabalin antibodies, which are capable of binding to pregabalin and its derivatives, which are coupled to particles, such as magnetic particles or particles suitable for separation by filtration, sedimentation, and/or other means. In some cases, a tracer, which can include a pregabalin derivative linked to a suitable chemiluminescent moiety, can be used to compete with free pregabalin in the patient's sample for the limited amount of anti-pregabalin antibody on the particle. After the sample, tracer, and antibody particles interact, a wash step can be used to remove unbound tracer. In certain instances, the amount of tracer bound to antibody particles can be measured by chemiluminescence, where chemiluminescence is expressed in Relative Light Units (RULE). The amount of chemiluminescence is inversely related to the amount of free drug in the patient's sample and concentration is determined by constructing a standard curve using known values of the drug.

Other Immunoassays for Pregabalin

The pregabalin derivatives, conjugates, antibodies, immunogens, and/or other conjugates described herein are also suitable for any of a number of other heterogeneous immunoassays with a range of detection systems including, but not limited to, enzymatic or fluorescent, and/or homogeneous immunoassays including, but not limited to, rapid lateral flow assays, and antibody arrays. While various immunodiagnostic assays have been described herein that utilize the pregabalin derivatives, conjugates, antibodies, immunogens and/or tracers, such assays can also be modified as desired. As such, various modifications of steps or acts for performing such immunoassays can be made within the scope of the present disclosure.

Kits

The present disclosure also provides kits that find use in practicing the subject methods, as described above. The kits of the present invention can include an anti-pregabalin antibody in a container, and may include a pregabalin conjugate (e.g., for use in a competitive binding assay, for use in an enzyme-based assay, and the like). The kits may also include a calibration standard and/or control standard useful in performing the assay; and, optionally, instructions on the use of the kit. Kit components can be in a liquid reagent form, a lyophilized form, or attached to a solid support. The reagents may each be in separate containers, or various reagents can be combined in one or more containers depending on cross-reactivity and stability of the reagents.

The sample, suspected of containing a pregabalin, and a calibration material, containing a known concentration of the pregabalin, can be assayed under similar conditions. Pregabalin concentration may then be calculated by comparing the results obtained for the unknown specimen with results obtained for the standard. In some cases, a calibration or dose response curve is used to compare the results obtained for the unknown specimen with results obtained for the standard.

Various ancillary materials may be employed in an assay in accordance with the present disclosure. In certain embodiments, buffers and/or stabilizers are present in the kit components. In certain embodiments, the kits include indicator solutions or indicator "dipsticks", blotters, culture media, cuvettes, and the like. In certain embodiments, the kits include indicator cartridges (where a kit component is bound to a solid support) for use in an automated detector. In certain embodiments, additional proteins, such as albumin, or surfactants, particularly non-ionic surfactants, may be included. In certain embodiments, the kits include an instruction manual that describes an assay method as disclosed herein and/or describes the use of the components of the kit.

Reagents and buffers used in the assays can be packaged separately or in combination into kit form to facilitate distribution. The reagents can be provided in suitable containers, and can be provided in a package along with written instructions relating to assay procedures.

In certain embodiments, a kit for determining the presence or the absence of pregabalin in a sample is provided. The kit may include an anti-pregabalin antibody and a pregabalin calibration standard. The pregabalin calibration standard may include calibration and control standards useful in performing the assay. The kits can also optionally include a conjugate of a pregabalin moiety and a detectable label. In certain embodiments, a detectable label of the conjugate is an enzyme. In certain embodiments, the enzyme is glucose-6-phosphate dehydrogenase (G6PDH). In some embodiments, the G6PDH is a variant of a naturally-occurring G6PDH in which one or more lysine residues are deleted or substituted, or one or more cysteine residues are introduced.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Also, it should be apparent that the embodiments can include additional embodiments not illustrated by example. Additionally, many of the examples have been performed with experimental protocols using the pregabalin derivatives, antigens, immunogens, and anti-pregabalin antibodies prepared in accordance with the present disclosure. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation of Amine Modified Pregabalin Derivative

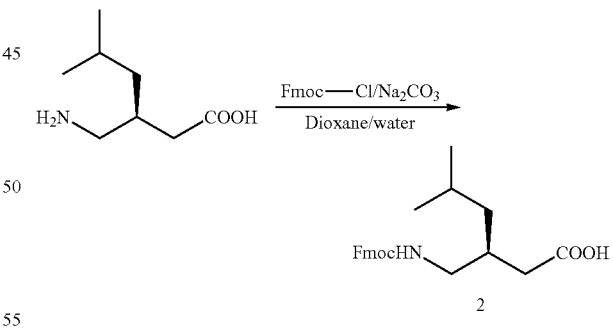

Pregabalin (396 mg, 2.5 mmol) was taken into a 10% aqueous solution of sodium carbonate (7 ml) and cooled in ice bath. A solution of Fmoc-Cl (647 mg, 2.5 mmol) in Dioxane (7 ml) was added drop wise. The reaction was allowed to warm up to room temperature and stirred for 2 hrs. Water (50 ml) was added and extracted with Ethyl Acetate (2×50 ml). The water layer was cooled in ice bath and acidified to pH=11 with concentrated HCl, then extracted with ethyl acetate (3×50 ml). The combined organic layer was washed with brine, dried over $MgSO_4$, and concentrated to give 1.1 g of crude product, which was purified on silica gel using Ethyl Acetate in Hexane (0 to 30%) to give 800 mg (84%) of clean desired intermediate 2.

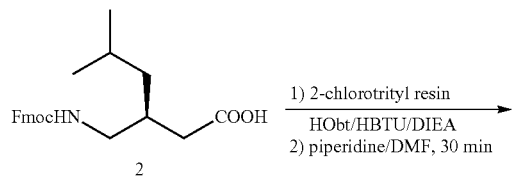

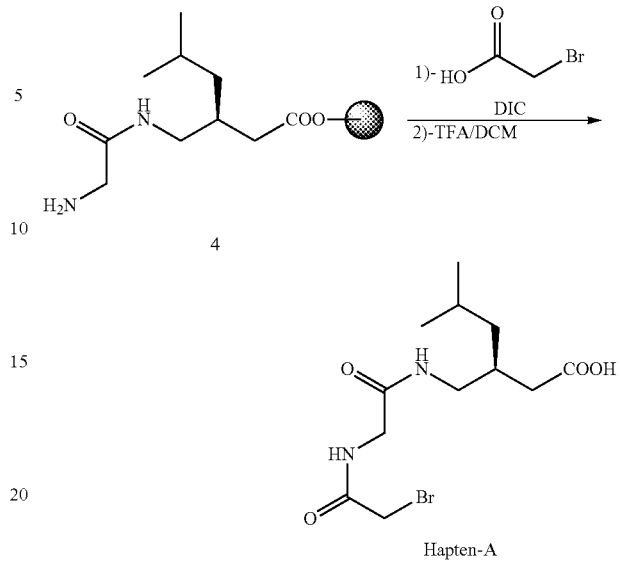

Hapten-A

Fmoc-pregabalin 2 (230 mg, 0.6 mmol) and DIEA (440 µl. 2.5 mmol) were mixed in dichloromethane (DCM; 10 ml) and added to 1 g of 2-Chlorotrityl resin (1 mmol/g). After one hour of shaking, methanol (2 ml) was added and the mix was shaken for 20 more minutes. Resin was drained, washed successively with DCM and DMF (3×10 ml each).

A solution of Piperidine in DMF (30%, 10 ml) was added to the resin and shaken for 30 minutes. The reactions was drained and washed as described above. The resin was dried under vacuum and used for the next step.

Fmoc-glycine (892 mg, 3 mmol) and HATU (1.14 g, 3 mmol) were added to a mixture of resin 3 in DMF (10 ml), DIEA (1.0 ml) was added and shaken for 4 hrs. This reaction was repeated twice. The resin was drained and washed with DMF, DCM and MeOH (3×30 ml each). A solution of Piperidine/DMF (30%, 10 ml) was added and shaken for 30 minutes. Resin was drained and washed as described above and dried under vacuum.

To a solution of 2-bromoacetic acid (556 mg, 4 mmol) in dry DMF (10 ml) was added DIC (626 µl, 4 mmol) and added to resin 4 (1.1 g). The mixture was shaken for 30 minutes. This reaction was repeated twice. Resin was drained and washed with DMF, DCM, and methanol (3×20 ml each). The resin was then dried under vacuum. The resin was taken in DCM (5 ml) and TFA (5 ml) was added and shaken for 1 hr. The resin was drained and washed with 20% TFA/DCM solution (10 ml). The combined drained and wash solution was evaporated to dryness and triturated with ether. The crude product was purified on silica gel using Methanol in DCM (0 to 10%) to give 115 mg of Hapten-A.

Mass; m/e=361.0 (100%), 363.0 (100%)

$^1$H NMR; 0.90 (d, 3H, J=6.4 Hz). 0.93 (d, 3H, J=6.4 Hz), 1.16 (m, 2H), 1.66 (m, 1H), 1.69 (dd, 1H, J=9.6, J=15.2 Hz), 2.25 (m, 1H), 2.39 (dd, 1H, J=2.4 Hz, J=15.2 Hz), 3.17 (m, 1H), 3.38 (m, 1H), 3.93 (s, 2H), 3.98 (t, 2H, J=5.6 Hz), 7.02 (ls, 1H), 7.45 (ls, 1H).

Example 2

Preparation of Carboxylic Acid Modified Pregabalin Derivative

Pregabalin (2 g, 12.5 mmol) was dissolved in a mixture of water (5 ml) and dioxane (10 ml) then 1N NaOH (2 ml) was added and cooled to 5° C. (ice bath). Bocanhydride (3 g, 14 mmol) was then added and stirred one hour in an ice bath. The reaction mixture was allowed to warm up to room temperature and stirred fore 16 hrs. Dioxane was evaporated under vacuum, Water (50 ml) was added and cooled in ice bath and acidified to pH=2-3. Extracted with ethyl acetate (3×50 ml). Organic layer was washed with water (30 ml), dried over MgSO4 and concentrated to give 3.1 g desired intermediate 5.

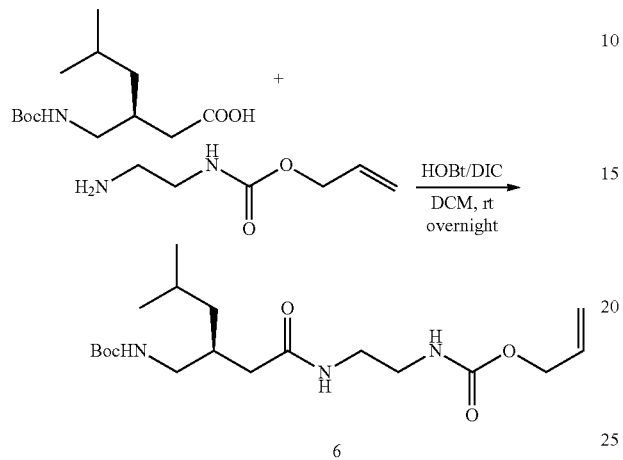

Intermediate 5 (200 mg, 0.77 mmol) was dissolved in DCM (10 ml). DIC (145 μl, 0.92 mmol) and HOBt (125 mg, 0.92 mmol) were added. After 5 min, at room temperature, Alloc-1,2-diaminoethane 1.2 (134 mg, 0.92 mmol) was added. After stirring for 16 hrs, solvent was evaporated, water (20 ml) was added and extracted with ethyl acetate (3×15 ml), washed with brine (15 ml) and dried over MgSO$_4$. After evaporation of solvent, 404 mg crude product was obtained, which was purified on silica gel using Methanol in DCM (0 to 5%) to give 200 mg (67%) of desired product 6.

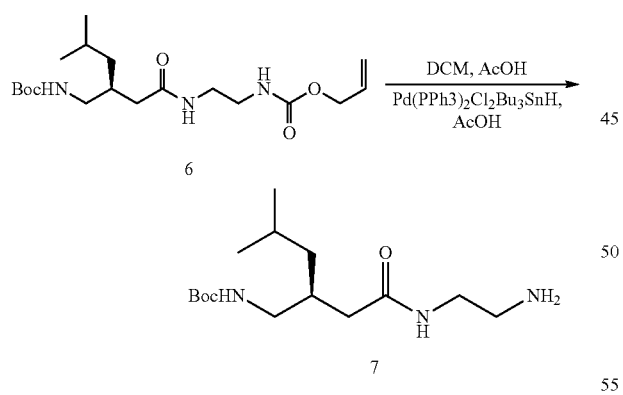

Intermediate 6 (194 mg, 0.50 mmol) was dissolved in DCM (10 ml). Dichlorobis(triphenylphosphine) palladium (II) (57 mg, 0.08 mmol) was added followed by Tributyltinhydride (200 μl, 0.75 mmol) and acetic acid (143 μl, 2.5 mmol). After overnight stirring, more palladium catalyst (42 mg, 0.05 mmol) was added and stirred for 4 hrs. No starting material was detected by TLC. Solvent was evaporated and the crude product was triturated in ether (2×20 ml) and decanted and the oily crude was left under high vacuum for 2 hrs. This material was then dissolved in DCM (10 ml) and hexane (20 ml) was added and left at 4° C. overnight. Solvent was decanted and the solid colorless precipitate left under vacuum to give 100 mg desired intermediate 7 pure enough to be used in the next step.

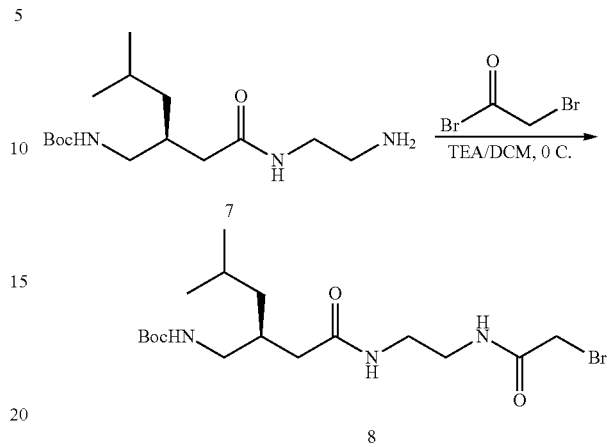

Intermediate 7 (100 mg, 0.33 mmol) in DCM (7 ml) was cooled in an ice bath and Triethyl amine (50 μl, 0.35 mmol) was added followed by Bromoacethyl bromide (67 μl, 0.33 mmol). The reaction mixture was stirred in ice bath for 20 minutes until no starting material left (monitored by TLC). Solvent was removed under vacuum, water (5 ml) was added and extracted with ethyl acetate (2×10 ml). Organic layer was dried over MgSO4 and concentrated to give 160 mg crude product, which was purified on silica gel using Ethyl Acetate/Hexanes (30% to 100%) to give 68 mg (50%) intermediate 8.

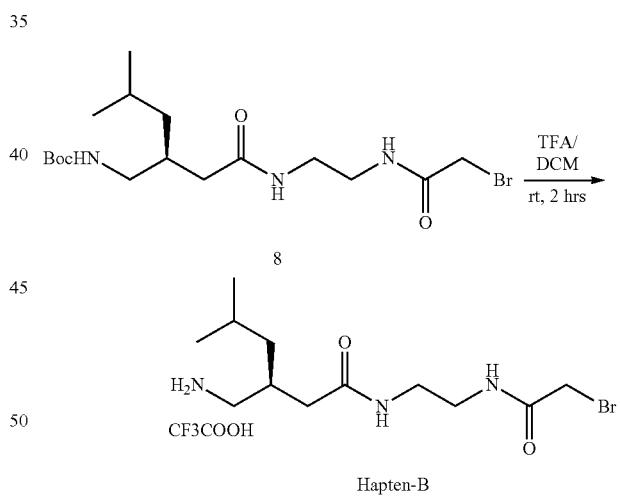

To a solution of intermediate 8 in DCM (4.5 ml), was added TFA (0.5 ml) at room temperature and stirred for 2 hrs. TLC showed no starting material. Solvent was evaporated under vacuum and the residue triturated with ether (10 ml). The residue was then left under vacuum to give 68 mg Hapten-B as a sticky solid.

Mass: m/e 322 (100% and 324 (100%), (M+1)

$^1$HNMR CDCl3, δ: 0.90 (d, 3H, J=6.8 Hz), 0.91 (d, 3H, J=6.8 Hz), 1.20 (t, 2H, J=7.6 Hz), 1.62 (m, 1H), 2.23 (m, 1H), 2.29 (dd, 1H, J=8.8 Hz, J=14.8 Hz), 2.39 (dd, 1H, J=4 Hz, J=14.8 Hz), 2.81 (dd, 1H, J=8 Hz, J=12.8 Hz), 3.00 (dd, 1H, J=3.2 Hz, J=12.8 Hz), 3.32 (m, 2H), 3.43 (m, 2H), 3.83 (s, 2H).

Example 3

Conjugation: Preparation of Pregabalin—SH-KLH Immunogen (KLH-A and KLH-B)

a) Preparation of Thiolated KLH (KLH-SH)

One vial of lyophilized KLH (Pierce, 21 mg) was reconstituted with 3 mL of phosphate buffer (0.1 M, 0.15 M NaCl, 1 mM EDTA, pH 8.0). The KLH solution was transferred to a reaction vial. Immediately before reaction, 6-8 mg of SATA (N-Succinimidyl-S-acetylthioacetate) was dissolved in 0.5 mL DMSO (resulted in ~55 mM solution). 30 µl of the SATA solution was combined with 3.0 mL of protein solution (7 mg/mL). The contents were mixed and reaction incubated at room temperature for at least 30 minutes. A Sephadex G-50 column was equilibrated with two column volumes of buffer (0.1 M phosphate, 0.15 M NaCl, pH 7.2-7.5). The reaction mixture was applied to column. Fraction (500 µL) was collected immediately. The fractions that contain protein were identified by measuring absorbance at 280 nm. Protein fractions were pooled to give 12 mL. Deacylation to generate a sulfhydryl for use in cross-linking was accomplished by adding 1.2 mL deacetylation solution (0.5 M Hydroxylamine, 25 mM EDTA in PBS, pH 7.2-7.5). Contents were mixed and reaction incubated for 2 hours at room temperature. Sephadex G-50 desalting column was used to purify the sulfhydryl-modified protein from the hydroxylamine in the deacetylation solution. The pooled fractions were concentrated to 2.6 mL (8 mg/mL) using Amicon concentrator. See FIG. 3.

b) Conjugation Hapten-A with Thiolated KLH (KLH-SH)

Dithiothreitol (DTT, 1 mM) was added to thiolated KLH to ensure reduction of disulfide bonds. The solution was allowed to mix overnight at 4° C. 10.2 mg Hapten-A was dissolved in 0.2 mL DMF. Pregabalin Hapten-A DMF solution was added in 5 to 10 µL quantities to a solution of thiolated KLH-SH. The reaction was continued overnight at 4° C. This solution was dialyzed against three changes (2.0 liter each) of HEPES buffer (10 mM, pH 7.0, 1 mM EDTA). This procedure yielded immunogen (KLH-A). See FIG. 5.

c) Conjugation Hapten-B with Thiolated KLH (KLH-SH)

Dithiothreitol (DTT, 1 mM) was added to thiolated KLH to ensure reduction of disulfide bonds. The solution was allowed to mix overnight at 4° C. 10.2 mg Hapten-B was dissolved in 0.2 mL DMF. Pregabalin Hapten-B DMF solution was added in 5 to 10 µL quantities to a solution of thiolated KLH-SH. The reaction was continued overnight at 4° C. This solution was dialyzed against three changes (2.0 liter each) of HEPES buffer (10 mM, pH 7.0, 1 mM EDTA). This procedure yielded immunogen (KLH-B). See FIG. 6.

Example 4

Conjugation: Native G6PDH and Pregabalin Containing Reactive Sulfhydryl Groups a) Preparation of Thiolated Native G6PDH (G6PDH-SH)

The N-succinimidyl S-acetylthioacetate (SATA) reagent described above was used to introduce protected sulfhydryls into native G6PDH. 21 mg G6PDH was dialyzed against phosphate buffer (0.1 M, 0.15 M NaCl, 1 mM EDTA, pH 8.0). The dialyzed G6PDH was transferred to a reaction vial. Immediately before reaction, 6-8 mg of SATA was dissolved in 0.5 mL of DMSO (resulted in ~55 mM solution). Combined was 3.0 mL of protein solution (7 mg/mL) with 30 µl of the SATA solution. The contents were mixed and reaction incubated at room temperature for at least 60 minutes. A 15 mL Sephadex G-50 column was equilibrated with two column volumes of buffer (0.1 M phosphate, 0.15 M NaCl, pH 7.2-7.5). The reaction mixture was applied to the column. 1 mL fractions were collected. Fractions that contain protein were identified by measuring for those peaks having absorbance at 280 nm. 9 mL sample volume was collected (approximating 21 mg enzyme). The enzyme was dialyzed against a bicarbonate buffer (100 mM, pH 9.0) to give free SH groups. See FIG. 4.

b) Conjugation Hapten-B with Thiolated Native G6PHD

The pH of the enzyme solution of (a) above was adjusted to 7.2 with 0.1M HCl. Pregabalin Hapten-B (11.8 mg) was dissolved in 200 µL DMF. Pregabalin Hapten-B DMF solution was added in 5 to 10 µL quantities to a solution of 21 mg thiolated G6PDH. The reaction was continued overnight at 4° C. This solution was dialyzed against three changes (2.0 liter each) of HEPES buffer (10 mM, pH 7.0, 1 mM EDTA). See FIG. 8.

Pregabalin Hapten-B is used in this Example. However, this conjugation technique is generally applicable to all Pregabalin Haptens containing bromoacetamido—such as Hapten-A.

Example 5

Conjugation: rG6PDH Containing Reactive Sulfhydryl Groups

Conjugation rG6PDH-SH was buffer exchanged with 50 mM phosphate-1.0 mM EDTA, pH 7.25. A solution of the protein (2 mL at 5 mg/mL) was then mixed with a dithio-erythreitol (25 mM final concentration in the phosphate-EDTA buffer) and mixture incubated at 4° C. for 16 hours. The protein solution was then buffer exchanged with 50 mM phosphate, 1.0 mM EDTA, 5 mM DTT, pH 7.25. The protein solution (2 mL at 5 mg/mL) was mixed with 40 fold molar excess of a DMF solution (0.05 mL) of Hapten-A and reaction mixture was stirred gently at 4° C. for 16 to 24 hours. Excess Hapten-A was separated from the enzyme-hapten conjugate by passing the reaction mixture over a column of Sephadex G 50 in 50 mM phosphate, pH 7.0. The column fractions containing the enzyme-hapten conjugate were pooled by measuring absorption at 280 nm. See FIG. 7.

Pregabalin Hapten-A was used in this Example. However, this conjugation technique was generally applicable to all Pregabalin Haptens to all Haptens Containing Reactive Bromoacetamido-Groups. Hapten-B can be used in this conjugation procedure. See FIG. 9.

Example 6

Preparation of Polyclonal Antibodies Reactive to Pregabalin

Polyclonal sera from 24 live rabbit were prepared by injecting the animal with immunogen KLH-A and a second set of 24 live rabbits were prepared by injecting the animal with immunogen KLH-B.

This immunogenic formulation included 200 µg of the immunogen for the first immunization and 100 µg for all subsequent immunizations. Regardless of immunogen amount, the formulation was diluted to 1 mL with sterile saline solution. This solution was then mixed thoroughly with 1 mL of the appropriate adjuvant: Freund's Complete Adjuvant for the first immunization or Freund's Incomplete Adjuvant for subsequent immunizations. The stable emulsion was subsequently injected subcutaneously with a 19×1½ needle into New Zealand white rabbits. Injections were made at 3-4 week intervals. Bleeds of the immunized rabbits were taken from the central ear artery using a 19×1 needle. Blood was left to clot at 37° C. overnight, at which point the serum was poured off and centrifuged. Finally, preservatives were added in order to form the polyclonal antibody material. Rabbit polyclonal antibodies to pregabalin produced by the above procedure were designated as #16203-16226. Rabbit polyclonal antibody #16209 (bleeds P7-19 were pooled) was used in examples below.

The pregabalin antibodies and enzyme conjugates may be employed in assays for the detection of pregabalin. Either of the immunogens (KLH-A), or (KLH-B) can be injected into a mouse, sheep or rabbit to raise antibody.

Rabbit polyclonal antibody #16209 (bleeds P7-19 were pooled) was screened for curve size, precision, and specificity. The obtained antibody was added into the antibody diluent to prepare the Antibody Reagent. The Antibody Reagent included antibody as prepared above, buffer, stabilizers, preservatives, and the substrates for the enzyme conjugate $NAD^+$ and glucose 6 phosphate. Enzyme Conjugate including G6PDH-B was added into the conjugate diluent to prepare the enzyme conjugate reagent. The enzyme Conjugate Reagent included the conjugate, buffer, stabilizers and preservatives. Enzyme conjugate G6PDH-B was used with rabbit polyclonal antibody #16209 (bleeds P7-19 were pooled) in examples below. This technique is generally applicable to produce polyclonal antibodies to pregabalin derivatives.

The pregabalin antibodies and enzyme conjugates may be advantageously used in a homogeneous assay format to detect pregabalin in samples. An analyzer (instrument) useful to set up the assay was the Siemens Viva-E® System. Pregabalin containing sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of $NAD^+$ to NADH, which can be measured at 340 nm. The change in the absorbance at 340 nm can be measured spectrophotometrically. The pregabalin concentration in a specimen can be measured in terms of G6PDH activity. The increase in the rate at 340 nm is due to the formation of NADH and is proportional to the enzyme conjugate activity.

Figure 11:
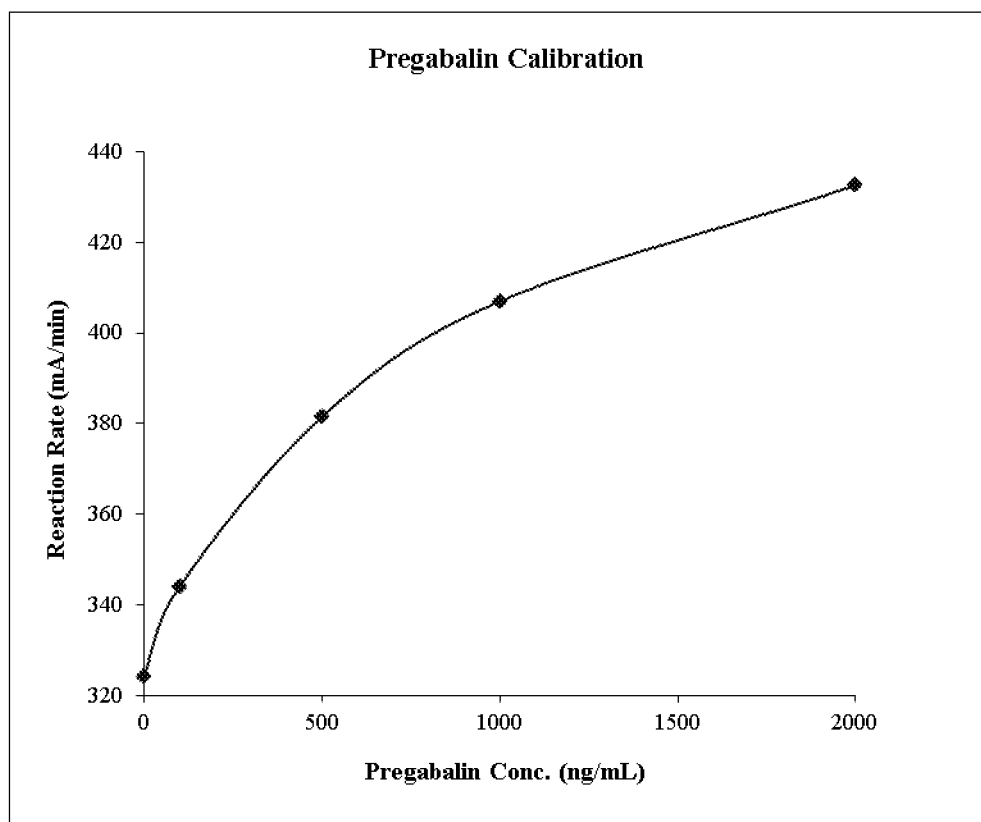
FIG. 11 is a calibration curve showing the change in optical density according to the concentration of pregabalin in a sample, according to embodiments of the present disclosure.

Using the above procedure, an assay calibration curve was generated (FIG. 11) using pregabalin spiked into pooled pregabalin-free human urine samples. The assay rate increased with increasing the concentration of free drug in the sample.

Example 7

Immunoassay

The pregabalin antibodies and enzyme conjugates may be employed in assays for the detection of the analyte. Either of the immunogens; KLH-A, or KLH-B, is injected into a mouse, rabbit or sheep to raise antibody. As described above, antibodies may be screened, and evaluated for properties such as specificity, conjugate inhibition, curve size and cross-reactivity. The obtained antibody is spiked into the antibody diluent to prepare the Antibody Reagent. The Antibody Reagent includes antibody as prepared above, buffer, stabilizers, preservatives, and the substrates for the enzyme conjugate $NAD^+$ and glucose-6-phosphate. Enzyme conjugate rG6PDH-A, or rG6PDH-B1 or rG6PDH-B2 or a label protein including alkaline phosphatase, B-galactosidase and horse radish peroxidase is spiked into the conjugate diluent to prepare the Enzyme Conjugate Reagent. The Enzyme Conjugate Reagent includes the conjugate, buffer, stabilizers and preservatives.

The pregabalin antibodies prepared as described in EXAMPLE 6 and enzyme conjugates prepared as described in EXAMPLE 4 or EXAMPLE 5 may be used in a homogeneous assay format to detect pregabalin in urine samples. An analyzer (instrument) useful to set up the assay is Siemens Viva-E. The Siemens Viva-E® System is an automated biochemistry analyzer used by medical and toxicology laboratories to process biological fluid specimens, such as urine, cerebrospinal fluid, and most commonly, blood. As illustrated in FIG. 10, pregabalin containing urine sample is incubated with Antibody Reagent followed by the addition of the Enzyme Conjugate Reagent. The enzyme conjugate activity decreases upon binding to the antibody. The enzyme conjugate, which is not bound to the antibody, catalyzes the oxidation of glucose-6-phosphate. The oxidation of glucose-6-phosphate is coupled with the reduction of $NAD^+$ to NADH, which can be measured at 340 nm. The change in the absorbance at 340 nm can be measured spectrophotometrically. The pregabalin concentration in a urine specimen can be measured in terms of G6PDH activity. The increase in the rate at 340 nm is due to the formation of NADH and is proportional to the enzyme conjugate activity. An assay curve can be generated using pregabalin spiked into pooled human pregabalin-free urine. The assay rate increases with increasing the concentration of free drug in the sample.

Example 8

Preparation Calibrators

Pooled pregabalin-free human urine samples were fortified with EDTA, and $NaN_3$ preservative. Pregabalin stock solution was obtained from Cerilliant Corporation, (P-066, Pregabalin 1.0 mg/mL). Pregabalin stock solution was added to the aliquots of pooled pregabalin-free human urine in preparing a series of known concentrations of pregabalin calibrators ranging from 0 to 2000 ng/mL. Table 1 below shows the concentrations of calibrators prepared by the aforementioned procedure.

TABLE 1

| Calibrator and Control Concentration Calibrator (ng/mL) |
| --- |
| 0 |
| 100 |
| 500 |
| 1000 |
| 2000 |

Example 9

Assay Performance
Standard Curve

Antibody Reagent was prepared by adding antibody #10930 to antibody diluent. The Antibody Reagent was assayed with Enzyme Conjugate Reagent prepared with rG6PDH-B2 enzyme conjugate. Calibration curves were generated on the Siemens Viva-E® System by assaying each level of calibrator in duplicate. Calibrators were prepared as described in EXAMPLE 8. An example of these calibrator rates is shown in Table 2 and a typical calibration plot is provided in FIG. 11.

TABLE 2

Calibrator Reaction Rate

| Pregabalin Concentration (ng/mL) | Reaction Rate (mA/min) Average of Duplicates |
|---|---|
| 0 | 324.3 |
| 100 | 344.0 |
| 500 | 381.5 |
| 1000 | 407.0 |
| 2000 | 432.5 |

Analytical Recovery

Pooled pregabalin-free human urine samples were fortified with EDTA, and NaN$_3$ preservative was aliquoted in 10 mL portions spiked with known quantity of pregabalin stock solution that was obtained from Cerilliant Corporation, as described in EXAMPLE 8. These samples were used to assess analytical recovery. Analytical recovery was evaluated using four samples. Testing was performed on the Siemens Viva-E® System as described in EXAMPLE 7. Two calibration curves were generated and 3 replicates of each sample were assayed each time with two runs. Mean, percent recovery and coefficient of variance (% CV) was calculated for each level. The coefficient of variation represents the ratio of the standard deviation to the mean, and it is a useful statistic for comparing the degree of variation from one data series to another. The coefficient of variation is reported as a percentage. Data are provided in Table 3.

TABLE 3

Analytical Recovery Data Summary

| Spiked Level (ng/mL) | Mean (ng/mL) | % CV | Recovery (%) |
|---|---|---|---|
| 200 | 197.9 | 2.4 | 99.0 |
| 400 | 378.3 | 3.5 | 94.6 |
| 800 | 778.6 | 2.8 | 97.3 |
| 1500 | 1361.2 | 4.1 | 90.7 |

Specificity of the Immunoassay

The 20 L-amino acids and gabapentin were tested due to their similar chemical structure to pregabalin.

The specificity of the immunoassay was evaluated by adding a compound to pooled pregabalin-free human urine samples fortified with EDTA, and NaN$_3$ preservative and testing the samples and determining the percent cross-reactivity. Separate stock solutions of each compound were prepared in methanol. Stock solution was added to pregabalin-free human urine to give the concentrations shown in Table 4. Testing was performed on the Siemens Viva-E® System as described in EXAMPLE 7. The percentage cross-reactivity was calculated for each compound tested. Results are shown in Table 4.

TABLE 4

Cross-Reactivity
% Cross-reactivity = 100 × (mean value Test − mean value Control) ÷ (Concentration Compound Tested)

| Compound | Concentration (µg/mL) | % Crossreactivity |
|---|---|---|
| Gabapentin | 200 | 0.019 |
| L-Arginine | 200 | 0.006 |
| L-Asparagine | 200 | 0.004 |
| L-Aspartic Acid | 200 | 0.004 |

TABLE 4-continued

Cross-Reactivity
% Cross-reactivity = 100 × (mean value Test − mean value Control) ÷ (Concentration Compound Tested)

| Compound | Concentration (µg/mL) | % Crossreactivity |
|---|---|---|
| L-Cysteine | 200 | 0.005 |
| L-Glutamic Acid | 200 | 0.006 |
| L-Glycine | 200 | 0.005 |
| L-Histidine | 200 | 0.007 |
| L-Isoleucine | 200 | 0.008 |
| L-Leucine | 200 | 0.038 |
| L-Methionine | 200 | 0.031 |
| L-Phenylalanine | 200 | 0.006 |
| L-Serine | 200 | 0.005 |
| L-Threonine | 200 | 0.005 |
| L-Tyrosine | 200 | 0.004 |
| L-Alanine | 200 | 0.004 |
| L-Lysine | 200 | 0.001 |
| L-Proline | 200 | 0.004 |
| L-Valine | 200 | 0.006 |
| L-Tryptophan | 200 | 0.006 |
| L-Glutamine | 200 | 0.004 |

The preceding merely illustrates the principles of embodiments of the present disclosure. It will be appreciated that those skilled in the art will be able to devise various arrangements which, although not explicitly described or shown herein, embody the principles of the embodiments of the present disclosure and are included within its spirit and scope. Furthermore, all examples and conditional language recited herein are principally intended to aid the reader in understanding the principles of the embodiments and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

What is claimed is:

1. A compound of Formula (A):

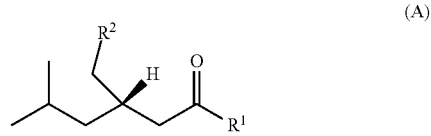

(A)

wherein
R$^1$ is —X—W-L-Z;
R$^2$ is —NH$_2$;
X is NH;
W is a bond;
L is a linker; and
Z is an enzyme;
wherein the linker is selected from the group consisting of —(CH$_2$)$_n$C(O)—, —C(O)(CH$_2$)$_n$—, —C(O)(CH$_2$)$_n$NH—C(O)—, —C(O)(CH$_2$)$_m$NH—C(O)(CH$_2$)$_n$—, —(CH$_2$)$_n$SCH$_2$C(O)—, —(CH$_2$)$_m$SCH$_2$C(O)(CH$_2$)$_n$—, —(CH$_2$)$_m$C(O)NH(CH$_2$)$_n$—, —(CH$_2$)$_n$ NH—C(O)—, —(CH$_2$)$_m$NH—C(O)(CH$_2$)$_n$—, —C(O)—(CH$_2$)$_n$—, and —(CH$_2$)$_n$—;
wherein m and n are each independently selected from an integer from 0 to 10,
or a salt thereof.

2. The compound of claim 1, wherein Z is an enzyme.

3. The compound of claim 2, wherein the enzyme is selected from the group consisting of glucose-6-phosphate dehydrogenase (G6PDH), alkaline phosphatase, β-galactosidase, and horse radish peroxidase.

4. The compound of claim 3, wherein the enzyme is glucose-6-phosphate dehydrogenase (G6PDH).

5. The compound of claim 1, wherein the linker is (CH$_2$)$_m$NH—C(O)(CH$_2$)$_n$—, wherein m is 2 and n is 1.

6. The compound of claim 4, wherein the G6PDH comprises at least one cysteine per subunit.

7. The compound of claim 6, wherein the cysteine is not native to a naturally-occurring G6PDH.

\* \* \* \* \*

UNITED STATES PATENT AND TRADEMARK OFFICE
CERTIFICATE OF CORRECTION

PATENT NO. : 10,690,687 B2
APPLICATION NO. : 15/936158
DATED : June 23, 2020
INVENTOR(S) : Valdez et al.

Page 1 of 1

It is certified that error appears in the above-identified patent and that said Letters Patent is hereby corrected as shown below:

In the Claims

At Column 59, Line 3, the recitation of "wherein in and n are each" should read -- wherein m and n are each --.

Signed and Sealed this
Eighteenth Day of August, 2020

Andrei Iancu
*Director of the United States Patent and Trademark Office*